US006451603B1

(12) United States Patent

Atkins et al.

(10) Patent No.: US 6,451,603 B1

(45) Date of Patent: *Sep. 17, 2002

(54) RIBOZYME NUCLEIC ACIDS AND METHODS OF USE THEREOF FOR CONTROLLING VIRAL PATHOGENS

(75) Inventors: David G. Atkins, Edgecliff; Wayne L. Gerlach, Killara, both of (AU); Mark J. Young, West Lafayette, IN (US)

(73) Assignee: Gene Shears Pty. Limited, Neutral Bay (AU)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/362,478

(22) PCT Filed: Jun. 29, 1993

(86) PCT No.: PCT/US93/06144

§ 371 (c)(1),
(2), (4) Date: Mar. 2, 1995

(87) PCT Pub. No.: WO94/00012

PCT Pub. Date: Jan. 6, 1994

(30) Foreign Application Priority Data

Jun. 29, 1992 (AU) .......................................... PL 3219/92

(51) Int. Cl.[7] ............................ C07H 21/04; C12Q 1/68

(52) U.S. Cl. ......................... 435/440; 435/6; 435/320.1; 435/455; 236/23.1; 236/23.2; 236/24.5

(58) Field of Search ........................... 435/6, 91.1, 91.3, 435/91.31, 91.33, 172.3, 240.1, 240.2, 240.4, 320.1, 440, 455; 536/23.1, 23.2, 24.5; 514/44

(56) References Cited

U.S. PATENT DOCUMENTS 5,324,643 A * 6/1994 Greatbatch et al. ....... 435/91.32

OTHER PUBLICATIONS

Agarwal, S. Antisense oligonucleotides: Towards Clinical Trials. TIBTECH vol. 14:376–387, Oct. 1996.*

Branch, A. A Good Antisense is Hard to Find. TIBS vol. 23: 45–50, Feb. 1998.*

A.G. Day et al., Proc. Natl. Acad. Sci USA 88:6721–6725 (1991).

F. Gadani et al., Archives of Virology 115:1–21 (1990).

R. Grumet, HortScience 25(5):508–513 (1990).

H. Homann et al., Nucleic Acids REsearch 21(12):2809–2814 (1993).

O.I. Miroshnichenko et al., Gene 84:83–89 (1989).

L. Ottavio et al., Virology 189:812–816 (1992).

M.A. Rezaian et al., Plant Molecular Biology 11:463–471 (1988).

J.J. Rossi et al., Pharmac. Ther. 50:245–254 (1991).

J.J. Rossi et al., Aids Research And Human Retroviruses 8(2):183–189 (1992).

K.B.G. Scholthof et al., Plant Physiol. 102:7–12 (1993).

T.I. Tikhonenko et al. Journal of Cellular Biochemistry, Supplement 15D p. 37 (1991).

M. Weerasinghe et al., Journal of Virology 65(10):5531–5534 (1991).

* cited by examiner

*Primary Examiner*—Sean McGarry
(74) *Attorney, Agent, or Firm*—John P. White; Cooper & Dunham LLP

(57) ABSTRACT

The invention consists of a non-naturally occurring nucleic acid molecule capable of blocking or interfering with a replicative intermediate of a virus, a virusoid, or a viroid. The nucleic acid molecule may contain a ribozyme or a plurality of ribozymes. Alternatively, the nucleic acid molecule may be an antisense nucleic acid molecule. The ribozyme may be a hairpin ribozyme, a hammerhead ribozyme, an RNAase P ribozyme, a minizyme, or other catalytic RNA molecule. The virus may be an animal, a mammalian, a plant, a fungal, a protozoan, a yeast, a bacterial virus, or a human virus. The nucleic acid molecule may be expressed in the cell or it may be preformed and administered ex vivo. The present invention contemplates methods of controlling infection of a pathogenic infectious agent in a plant or animal.

16 Claims, 13 Drawing Sheets

Cumulative constructs vs. CEV +ve strand

Rz TC1 TMV vs CEV

Legend:
- ■ CEV 37
- □ CEV 50
- ♦ TMV 37
- ◊ TMV 50

X-axis: Incubation Time (minutes)
Y-axis: % Cleavage

RIBOZYME NUCLEIC ACIDS AND METHODS OF USE THEREOF FOR CONTROLLING VIRAL PATHOGENS

Throughout this application various publications are cited within parenthesis. Full bibliographic citations for these references may be found listed alphabetically at the end of the specification immediately preceding the claims. The disclosures for these publications in their entireties are hereby incorporated by reference into this application to more fully describe the state of the art to which this invention pertains.

BACKGROUND OF THE INVENTION

The present invention relates generally to the control of pathogens in plants and animals and more particularly to the control of viruses and viroids in transgenic plants. Further, it relates to the control of viral pathogens in mammals.

The ability to control plant pathogens has long been a principal goal in agricultural research. In contemporary research, there has been a focus on recombinant DNA technology in the quest for developing disease-resistant plants. However, despite the commercially devastating effects of various diseases in, for example, crop plants, little progress has been made in controlling viroid and virus infection in plants.

A viroid is a plant-pathogenic infectious agent comprising a naked (i.e. non-protein associated) circular single stranded RNA molecule. Most known viroids are similar in structure and apparently rely solely on host cell enzymes for replication. Replication is thought to occur in the host cell nucleus where the RNA is associated with the nucleolus. Infectious viroid RNA (+) is transcribed into an oligomeric complementary RNA (−) several times the unit length of the viroid (+) RNA. The (−) RNA oligomers probably then serve as templates for the synthesis of (+) RNA which is then cleaved into unit-length linear strands followed by ligation to form single stranded infectious (+) RNA molecules.

The viroid class of plant pathogens are low molecular weight, circular, single-stranded RNA molecules. They are the smallest known autonomously replicating agents with a size range between 246–375 nucleotides. The RNA has been shown in have extensive intramolecular base-pairing giving the viroids a rod-like structure (Sanger et al., 1976). The result of the interaction of the viroids with the plant host can range from no apparent or a mild associated host phenotype to an extremely severe pathology. In many cases the infection can lead to significant impairment of the plant growth and fruiting causing economically important disease. Although the pathology of viroid infections has been well documents, there has been no report of the identification of resistance genes of the design and introduction of synthetic resistance genes into host plants. A contributing factor to this is that details of the mechanisms and onset of pathogenesis are not well understood. As such, it is difficult to identify host gene targets to breed for a resistant genotype. A potentially useful approach to bypass this problem and to lead to the development of viroid-resistant cultivars is the application of the concept of pathogen-derived resistance mechanisms (Sanford and Johnston, 1985).

Pathogen-derived resistance includes strategies which involve the expression of a component of the pathogen in transgenic hosts resulting in increased tolerance or resistance in the host when infected with that pathogen. Pathogen-derived resistance has been applied to a wide range of plant virus and host combinations. Some of the successful methods involving the expression of virus open reading frames (ORF) in transgenic plant hosts include the expression of virus capsid protein genes (for review see Beachy et al., 1990) and, in the case of Tobacco Mosaic Virus and Pea Early Browning Virus, the expression of the readthrough sequence of the virus-encoded RNA polymerase gene (Golemboski et al., 1990, Macfarlane and Davies, 1992). Although very effective against viruses, these techniques are unsuitable for application to viroids as they do not have identifiable ORFs (Sanger, 1987). However, the fact that the viroids are single-stranded RNA molecules makes them potentially sensitive to resistance strategies involving the expression of transgenes encoding either antisense or ribozyme RNA molecules. These gene manipulation techniques that result in regulation most likely via a primary interaction between the transgene transcript and a target RNA molecule have been shown to be extremely effective in plants. Antisense-mediated control of gene expression has been demonstrated for endogenous plant genes in the case of inhibition of a number of endogenous genes. In addition, antisense strategies have been successful in conferring a degree of resistance to the viral pathogens potato virus X; cucumber mosaic virus and potato leafroll virus (Hemenway et al., 1988, Cuozzo et al., 1988; Kawchuk et al., 1991) in the appropriate plant hosts. Ribozyme-mediated gene inactivation strategies have been employed against the bacterial neomycin phosphotransferase gene in protoplasts of *Nicotiana tabacum* (Steinecke et al., 1992) and TMV replication in protoplasts (Edington and Nelson, 1992). As yet, neither technique has been evaluated against the viroid class of pathogens.

This application describes the first reported test of these strategies to engineer resistance to viroids. The experimental system involved the well characterized Citrus Exocortis Viroid and the readily transformable tomato host, *Lycopersicon lycopersicum* cv. UC82B. The combination of the CEV Australian isolate (CEV A, Visvader et al., 1982) and the *Lycopersicon lycopersicum* UC82B cultivar was chosen as the productive infection. Although this viroid and host combination results in viroid replication to the same level as infection of the symptom-showing host *L. lycopersicum* Mill cv. Rutgers, the interaction produces negligible symptoms and allows assessment of viroid replication independently of the devastating symptoms seen in the latter cultivar. The strategies which were tested involved the expression of transgenes encoding antisense and long ribozyme genes targeting either the viroid-sense (positive strand) RNA molecule or the complementary (negative strand) viroid RNA. The rationale for the selection of two target RNAs was that it is possible that the positive and negative strand RNAs may represent quite different targets in terms of abundance, cellular localization and/or structure.

Although the full details of the viroid replication cycle have not been elucidated it is generally accepted that the replication cycle involves the synthesis of the negative strand template. From this negative strand, copies of positive strand molecules are formed which are subsequently processed into circular viroid molecules (Symons, 1990). For CEV it has been reported that the negative strand is much less abundant than the positive strand in infected plants and that the distribution of RNA, in terms of multimeric units, is different for the two RNA species (Hutchins et al., 1985).

Although the exact cause of the pathogenicity of viroids is yet to be established, it is possible that the viroids interfere with pre-RNA processing in host cells. The result in an array of symptoms ranging from mild (e.g. discoloration and malformation of leaves) to severe and lethal.

There is a need, therefore, to develop a method for effectively controlling infection of viroids, viruses, and other viroid-like infectious agents in plants. In addition, there is a need for methods for controlling virus pathogens of animals.

SUMMARY OF THE INVENTION

The invention consists of a non-naturally occurring nucleic acid molecule capable of blocking or interfering with a replicative intermediate of a virus, a virusoid, or a viroid. The nucleic acid molecule may contain a ribozyme or a plurality of ribozymes. Alternatively, the nucleic acid molecule may be an antisense nucleic acid molecule. The ribozyme may be a hairpin ribozyme, a hammerhead ribozyme, an RNAase P ribozyme, a minizyme, or other catalytic RNA molecule.

The virus may be an animal, a mammalian, a plant, a fungal, a protozoan, a yeast, a bacterial virus, or a human virus. The nucleic acid molecule may be expressed in the cell or it may be preformed and administered ex vivo.

The present invention contemplates a methods of controlling infection of a pathogenic infectious agent in a plant or animal.

BRIEF DESCRIPTION OF THE FIGURES

FIG. 7A shows the result of probing with CEV cDNA. FIG. 7B shows a duplicate series of nucleic acid samples probed with the rDNA probe pTA71 to determine the variation in loading levels of the nucleic acid. Lanes 1 and 2 are RNA samples from uninoculated transgenic plants and lanes 3–12 are samples from 10 CEV-inoculated transgenic tomato plants.

FIG. 8A, plants expressing antisense targeting the negative CEV RNA strand [As(−)#1, As(−)#2, As(−)#3]; FIG. 8B, plants expressing long ribozymes targeting the negative CEV RNA [3Rz(−)#1, 3Rz(−)#2, 4Rz(−)]; FIG. 8C, plants expressing antisense to the positive CEV RNA [As(+)#1, As(+)#2]; FIG. 8D, plants expressing long ribozymes targeting the positive CEV RNA [3Rz(+)#1, 3Rz(+)#2, 3Rz(+)#3].

DETAILED DESCRIPTION OF THE INVENTION

Figure 1:
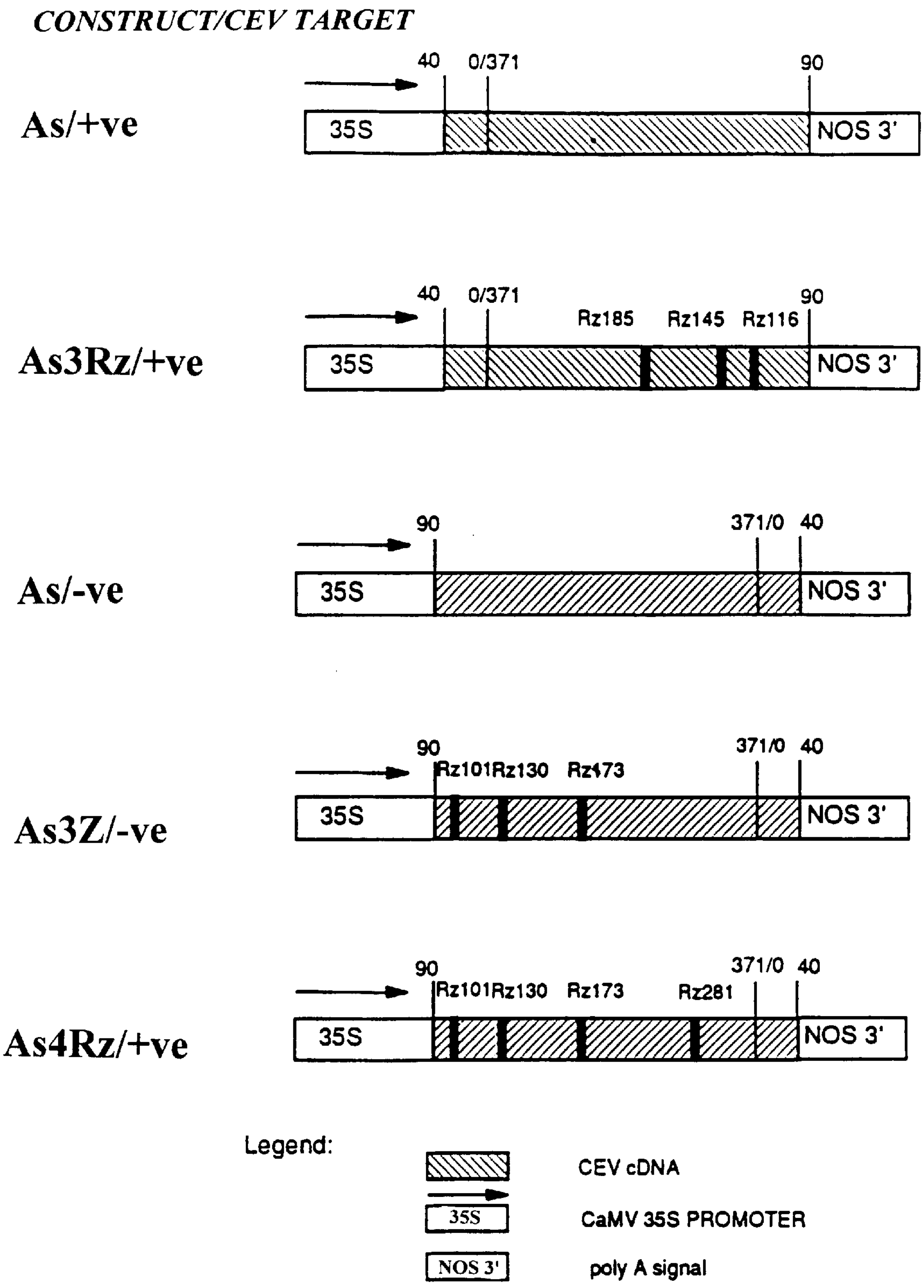
FIG. 1 is a diagrammatic representation of genes used to transform *Lycopersicon lycopersicum* UC82B to confer resistance to CEV infection. The Figure shows the inserts in the vector pGA470. Structures of the five chimeric genes constructed for plant transformation to produce antisense or long ribozymes complementary to either the CEV positive or negative RNA strands. The CEV cDNA fragment used in all constructs, in the orientation depending on the required sense transcript, was the full-length sequence with a deletion between bases 40 and 90. The positions of the ribozymes are indicated and the number of the base in the target RNA at which cleavage occurs in the 3' is shown. Abbreviations: AS: anti-sense; +Ve: viroid (+) RNA; +Ve; viroid (−) RNA; $R_Z$101: ribozyme targeting CEV nucleotide number 101. The CaMV 35S promoter and nos 3' processing sequences are indicated.

The invention consists of a non-naturally occurring nucleic acid molecule capable of blocking or interfering with a replicative intermediate of a virus, a virusoid, or a viroid. The nucleic acid molecule may contain a ribozyme or a plurality of ribozymes. Alternatively, the nucleic acid molecule may be an antisense nucleic acid molecule. For example the ribozyme may be a hairpin ribozyme, a hammerhead ribozyme, an RNAase P ribozyme, a minizyme (McCall, 1992), or other catalytic RNA molecule.

The target (−) RNA molecule is generally formed during the replication cycle of a viroid. Although not wishing to limit the present invention to any one theory as to the mode of action, it is possible the second nucleic acid molecule forms a duplex with the (−) RNA thus preventing or reducing (+)RNA synthesis and/or preventing or otherwise interfering with polymerase binding. A number of other mechanisms of action, however, are also possible such as the competition for other host enzymes.

Since the exact mode of action is unknown, the effect is said to "control infection" which means it interferes with the virus or viroid itself or its replication cycle thereby limiting the extent to which the virus or viroid can replicate and spread or even maintain itself at constant levels thereby ameliorating the effects of infection.

The virus may be an animal, a mammalian, a plant, a fungal, a protozoan, a yeast, a bacterial virus, or a human virus. The virus may be a picornavirus, a calicivirus, a togavirus, a flavirus, a coronavirus, a rhabdovirus, a filovirus, a paramyxovirus, an orthomyxovirus, a bunyavirus, an arenavirus, a poliovirus, a coxsackie virus, an enterovirus such as human enterovirus, bovine enterovirus, porcine enterovirus, a rhinovirus such as human rhinovirus, bovine rhinovirus, equine rhinovirus, a foot-and-mouth disease virus, an encephalitis virus, a rabies virus, a hog cholera virus, a yellow fever virus, a human corona virus, a canine corona virus, a calf corona virus, a rabies-like virus, a measles-like virus, a parainfluenza virus, a mumps virus, a measles virus, canine distemper virus, an influenza virus such as influenza A, B, C, of humans, swine, horses or fowl, an infectious hematopoietic virus of fish, or an infectious pancreatic virus of fish.

The plant virus may be a tobamovirus, a tobravirus, a hordevirus, a potexvirus, a carlavirus, a potyvirus, a closterovirus, a tymovirus, a tombusvirus, a sobemovirus, or a luteovirus. The plant virus may be a potato yellow dwarf virus, a cucumber mosaic virus, a tomato spotted wilt virus, a tomato mosaic virus, a potato virus X (PVX), a potato virus Y (PVY), a carnation latent virus, a tomato rattle virus, a pea early browning virus, a barley stripe mosaic virus, a turnip yellow mosaic virus, a barley yellow dwarf virus, a beet yellows virus, a potato leaf roll virus, a tomato bushy stunt virus, a southern bean mosaic virus, a maize chlorotic virus, beet necrotic yellow vein virus, or a tobacco necrosis virus.

The viroid may be avocado sunblotch viroid (ASBV), burdock stunt viroid (BSV), chrysanthemum chlorotic mottle viroid (CCMV), chrysanthemum stunt viroid (CSV), citrus exocortis viroid (CEV), coconut cadang-cadang viroid (CCCV), cucumber pale fruit viroid (CPFV), hop stunt viroid (HSV), potato-spindle tuber viroid (PSTV), tomato bunch top viroid (TBTV), or tomato "planta macho" viroid (TPMV).

The DNA molecule codes for the nucleic acid molecule, a transfer vector comprises of RNA or DNA or a combination thereof containing a nucleotide sequence which on transcription gives rise to above-mentioned non-naturally occurring nucleic acid molecule.

The process by which a plant or animal is rendered resistant to viral infection comprises introducing into the plant or animal a construct which on transcription gives rise to the above-mentioned nucleic acid molecule. The introduction of the nucleic acid molecule is made by genetic transformation of a part of the plant by a DNA sequence coding for the nucleic acid molecule, followed by the regeneration of a transgenic plant. The transformation is carried out by the intermediary of *Agrobacterium tumefaciens* or *Agrobacterium rhizogenes*.

The present invention is further directed to a DNA cassette for a plant, said cassette comprising a genetic sequence and a promoter capable of directing expression of said genetic sequences wherein said genetic sequence on expression provides anti-sense or ribozyme RNA to (−) RNA or a portion thereof associated with a viroid. The DNA cassette may further be part of a DNA transfer vector suitable for transferring the DNA cassette into a plant cell and insertion into a plant genome. In a most preferred embodiment of the present invention, the DNA cassette is carried by broad host range plasmid pGA470 and which is capable of transformation into plant cells using *Agrobacterium*. The present invention, however, extends to other means of transfer such as genetic bullets (e.g. DNA-coated tungsten particles, high-velocity micro projectile bombardment) and electroporation amongst others (Maliga, 1993; Bryant, 1992; or Shimamoto, 1989).

The transgenic plant resistant to a virus characterized in that it contains in its genome a sequence which gives rise, on transcription, to the nucleic acid molecule mentioned above. This transgenic plant, including fruits, and seeds thereof, may be from alfalfa, apple, bean, canola (oilseed rape), cantaloupe, corn, cotton, courgette, cucumber, melon, papaya, pepper, potato, rice, soybean, squash, strawberry, sunflower, sweet pepper, tobacco, tomato, or walnut. Also included are the plant cells transformed by the above-mentioned transfer vector, as well as a prokaryotic or eukaryotic cell, plant or animal, comprising a nucleotide sequence which is, or on transcription gives rise to, nucleic acid molecule.

The invention also provides a method of interfering with the replication of an RNA virus having a replicative strand which comprises contacting a cell with a nucleic acid molecule capable of hybridizing with the replicative strand or with a ribozyme capable of cleaving the replicative strand so as to thereby interfere the replication of the RNA virus in that cell.

The present invention contemplates a method of controlling infection of a pathogenic infectious agent in a plant or animal comprising generating a transgenic plant or animal which synthesizes an effective amount of a nucleic acid molecule capable of interfering with replicative intermediate of said infectious agent.

More particularly, the present invention provides a method of controlling infection of a pathogenic infectious agent in a plant or animal comprising generating a transgenic plant or animal carrying a first nucleic acid molecule with a nucleotide sequence which, on transcription, provides a second nucleic acid molecule which is substantially antisense to at least a portion of a replicative intermediate associated with said infectious agent.

The present invention is particularly directed to viroids as the infectious agents but also extends to all pathogens in which there is associated a (−) RNA or equivalent molecule during their replication cycle. Accordingly, by "associated" means that the infectious agent comprises (−) RNA or that (−) RNA is formed at some point during its life cycle such as during the replication cycle.

The transgenic plant is generally made by inserting a genetic sequence in the form of DNA into the genome of a plant cell and re-generating a plant therefrom. The genetic sequence thus constitutes the first nucleic acid molecule referred to above. The "genome" includes chromosomal DNA and extrachromosomal DNA.

The genetic sequence is required to be expressible either constituitively or in response to natural stimuli or artificially provided stimuli. The promoter directing expression of the genetic sequence may, therefore, be naturally occurring within the plant genome or may be associated with the genetic sequence before insertion into the genome. One preferred promoter is the 355 promoter such as is present on expression vectors pJ35SN and pGA470. For other techniques and viral hosts see U.S. Pat. No. 5,107,065.

Expression of the genetic sequence in the plant cell gives rise to a transcript which comprises the second nucleic acid molecule referred to above. The nucleotide sequence of at least a portion of the molecule is complementary to the nucleotide sequence of a (−) RNA associated with a target viroid. The second nucleic acid molecules may also be a ribozyme (i.e., long ribozyme) molecule. The anti-sense or long ribozyme second nucleic acid molecule or a portion thereof may also be translated into polypeptide as well as acting as an anti-sense or catalytic molecule.

The invention also contemplates a method of producing a nonhuman animal which comprises introducing into at least some cells of a recipient animal a vector comprising the nucleic acid molecule mentioned above, the gene being operably linked to a promoter that is functional in at least some of the cells into which the vector is introduced, such that a genetically modified animal is obtained which can express the nucleic acid molecule.

In one embodiment, the construct is cloned in a plasmid. Various plasmids well known to a skilled practitioner will serve this purpose. One method is to clone and express the nucleic acid molecule capable of inhibiting the replicative intermediate under a strong promoter such that large amount of RNA against the replicative intermediate of the virus will be produced. In a preferred embodiment, the construct also includes a selectable marker gene.

Typical strong mammalian promoters include an adenovirus promoter, an simian virus 40 (SV40) promoter, a cytomegalovirus promoter, a mouse mammary tumor virus (MMTV) promoter, a Malony murine leukemia virus promoter, a murine sarcoma virus promoter, and a Rous sarcoma virus promoter. Also suitable as a promoter is an animal cell promoter such as an interferon promoter, a metallothionein promoter, an immunoglobulin promoter.

Various drug resistance genes are examples of selectable marker genes. Some of the drug resistant genes are neomycin resistant gene and dihydrofolate reductase which can be selected by methotrexate. Other selectable marker genes include thymidine kinase gene, adenine phosphoribosyl transferase gene, hypoxanthine-guanine phosphoribosyl transferase gene.

The introduction of the modified gene to the genome of the animal comprises microinjection of the construct into the egg or embryo; electroporation of the construct into the mouse egg or embryo or other techniques of introduction known to an ordinary skilled in the art.

In some situations, embryonic stem cells are cultured in vitro and introduced into the blastocytes. The construct may be introduced to the animal by the embryonic stem cell.

In a preferred embodiment, the construct is cloned in a cloning vehicle. Such vehicle may be a plasmid, bacteriophage, other virus or the like known to the ordinary skilled in the art. The final selected modified embryonic stem cell line is microinjected into the blastocyte of a developing embryo. Alternatively, the plasmid containing construct and the selection marker gene transforms stem cells directly and the transformed stem cells are selected for the selection marker phenotype.

In the present invention the nonhuman animal and progeny thereof contain at least some cells that retain the nucleic acid molecule capable of blocking or interfering with the replicative strand in expressible form. The transgenic nonhuman animal all of whose germ and somatic cells contain a non-naturally occurring nucleic acid molecule capable of interfering with the replicative strand of a virus in expressible form introduced into said animal, or an ancestor thereof, at an embryonic stage as described in U.S. Pat. Nos. 4,736,866, 5,175,383, 5,175,384, or 5,175,385. See also (Van Brunt, 1988; Hammer, 1985; Gordon et al., 1987; Pittius et al., 1988; Simons et al. 1987; Simons et al., 1988).

The invention also includes a process for rendering cells resistant to viral infection which comprises treating the cells with the nucleic acid molecule described above. Preferably, the treatment is ex vivo. In addition as used herein the terms antisense and ribozymes also include compounds with modified nucleotides, deoxynucleotides, peptide nucleic acids, etc. These would be used for ex vivo treatment or topical treatment.

An effective amount of the nucleic acid molecule of the present invention would generally comprise from about 1 nM to about 1 mM concentration in a dosage form, such as a cream for topical application, a sterile injectable composition, or other composition for parenteral administration. In respect of topical formulations, it is generally preferred that between about 50 $\mu$M to about 500 $\mu$M nucleic acid molecule be employed. Compounds comprising nucleotide derivatives, such derivatives may involve chemically modified groups, such as phosphorothioate or methyl phosphonate derivatives may be active in nanomolar concentrations. Such concentrations may also be employed to avoid toxicity.

Therapeutic strategies involving treatment of disease employing compounds of this invention are generally the same as those involved with antisense approaches, such as described in the anti-sense bibliography of (Chrisley, 1991). Particularly, concentrations of compounds utilized, methods and modes of administration, and formulations involved may be the same as those employed for antisense applications.

An "effective amount" as used herein refers to that amount which provides a desired effect in a mammal having a given condition and administration regimen. Compositions comprising effective amounts together with suitable diluents, preservatives, solubilizers, emulsifiers, adjuvants and/or carriers useful for therapy. Such compositions are liquids or lyophilized or otherwise dried formulations and include diluents of various buffer content (e.g., Tris-HCL, acetate phosphate), pH and ionic strength, additives such as albumin or gelatin to prevent absorption to surfaces, detergents (e.g., Tween 20, Tween 80, Pluronic F68, bile acid salts), solubilizing agents (e.g., Thimerosal, benzyl alcohol), bulking substances or tonicity modifiers (e.g., lactose, mannitol), covalent attachment of polymers such as polyethylene glycol to the nucleic acid molecule, complexation with metal ions, or incorporation of the material into or onto particulate preparations of polymeric compounds such as polylactic acid, polyglycolic acid, polyvinyl pyrrolidone, etc. or into liposomes, microemulsions, micelles, unilamellar or multilamellar vesicles, erythrocyte ghosts, or sphereoplasts. Such compositions will influence the physical state, solubility, stability, rate of in vivo release, and rate of in vivo clearance of the oligonucleotide. Other ingredients optionally may be added such as antioxidants, e.g., ascorbic acid; low molecular weight (less than about ten residues) polypeptides, i.e., polyarginine or tripeptides; proteins, such as serum albumin, gelatin, or immunoglobulins; amino acids; such as glycine, glutamine acid, aspartic acid, or arginine; chelating agents such as EDTA; and sugar alcohols such as mannitol or sorbitol. Possible sustained release compositions include formulation of lipophilic depots (e.g., fatty acids, waxes, oils). Also comprehended by the invention are particulate compositions coated with polymers (e.g., polyoxamers or polyoxamines) and nucleic acid molecules coupled to antibodies directed against tissue-specific receptors, ligands or antigens or coupled to ligands of tissue-specific receptors. Further, specific nucleotide sequences may be added to target the nucleic acid molecule of this invention to the nucleus, plastid, cytoplasm or to specific types of cells. Other embodiments of the compositions of the invention incorporate particulate forms protective coatings, protease inhibitors or permeation enhancers for various routes of administration, including parenteral, pulmonary, nasal and oral.

Suitable topical formulations include gels, creams, solutions, emulsions, carbohydrate polymers, biodegradable matrices thereof; vapors, mists, aerosols, or other inhalants. The nucleic acid molecules may be encapsulated in a wafer, wax, film or solid carrier, including chewing gums. Permeation enhancers to aid in transport to movement across the epithelial layer are also known in the art and include, but are not limited to, dimethyl sulfoxide and glycols.

Ribonucleotide and deoxyribonucleotide derivatives or modifications are well known in the art, and are compatible with commercially available DNA synthesizers. (See Saenger, 1984, particularly pages 159–200). Nucleotides comprise a base, sugar and a monophosphate group. Accordingly, nucleotide derivatives, substitutions, or modifications may be made at the level of the base, sugar, or monophosphate.

A large number of modified bases are found in nature, and a wide range of modified bases have been synthetically produced (Saenger, 1984; and CRC Handbook of Biochemistry). Suitable bases would include inosine, 5'-methylcytosine, 5'-bromouracil, xanthine, hypoxanthine and other such bases. For example, amino groups and ring nitrogens may be alkylated, such as alkylation of ring nitrogen atoms or carbon atoms such as $N^1$ and $N^7$ of guanine and $C^5$ of cytosine; substitution of keto by thioketo groups; saturation of carbon=carbon double bonds, and introduction of a C-glycosyl link in pseudouridine. Examples of thioketo derivatives are 6-mercaptopurine and 6-mercaptoguanine.

Bases may be substituted with various groups, such as halogen, hydroxy, amine, alkyl, azido, nitro, phenyl and the like. Bases may be substituted with other chemical species, such as an amido-acid side chain or linkers which may or may not incorporate other chemical entities, e.g. acidic or basic groups. For example, guanine ($G_3$) may be substituted with tyrosine, and cytosine (C1) or adenine (A11) similarly substituted with histidine.

The sugar moiety of the nucleotide may also be modified according to well known methods in the art (Saenger, 1984). This invention embraces various modifications to the sugar moiety of nucleotides as long as such modifications do not abolish cleavage activity of the compound. Examples of modified sugars include replacement of secondary hydroxyl groups with halogen, amino or azido groups; 2'-methylation; conformational variants such as the $O_2$'-hydroxyl being cis-oriented to the glycosyl $C_1$, -N link to provide arabinonucleosides, and conformational isomers at carbon $C_1$, to give $\alpha$-nucleosides, and the like. Further, non ribose sugars may be used such as hexoses such as glucose, pentoses such as arabinose.

The phosphate moiety of nucleosides is also subject to derivatisation or modifications, which are well known in the art. For example, replacement of oxygen with nitrogen, sulphur or carbon derivatives to respectively give phosphoramidates, posphorothioates, phosphodithiolates, and phosphonates. Substitutions of oxygen with nitrogen, sulphur of carbon derivatives may be made in bridging or non bridging positions. It has been well established from work involving antisense oligonucleotides that phosphodiester and phosphorothioate derivatives may efficiently enter cells (particularly when of short length), possibly due to association with a cellular receptor. Methylphosphonates are probably readily taken up by cells by virtue of their electrical neutrality.

The phosphate moiety may be completely replaced with peptide nucleic acids (see Hanvey et al., 1992; Nielson, 1991; and Egholm, 1992). Other replacements are well-known to those skilled in the art for example siloxane bridges, carbonate bridges, acetamidate bridges, carbamate bridges, thioether bridges, etc. (Uhlmann and Peymann, 1990).

The present invention is further described by reference to the following non-limiting Figures and Example.

EXPERIMENTAL DETAILS

Materials and Methods:

The present invention was exemplified using a line of tomato, *Lycopersicon lycopersicum*, UC82B. The strain of tomato is routinely used for transformation and, as with several other lines of tomato, will support the replication of the viroid pathogen Citrus Exocortis Viroid (CEV). Inoculation of UC82B seedlings with infectious CEV RNA (CEV A, Australian isolate) results in the accumulation of intracellular viroid RNA an can lead to the development of mild symptoms such as epinasty and stunting.

Five different gene constructions were introduced into *L. lycopersicum* (FIG. 1). The constructs were of the antisense (As) of ribozyme-containing antisense type (catalytic antisense). The specific constructs that were prepared were as follows:

(a) Antisense targeting the viroid-sense RNA strand (positive RNA strand).

(b) Long ribozymes containing three ribozymes targeting the positive RNA strand.

(c) Antisense targeting the negative RNA strand (RNA strand complementary to the viroid-sense RNA).

(d) Long ribozymes containing three ribozymes targeting the negative RNA strand.

(e) Long ribozymes containing four ribozymes targeting the negative RNA strand.

The As and Catalytic As constructs were derived from a cDNA clone comprising the full 371 bp of the CEV genome. The full-length genomic cDNA was cloned as a BamHI restriction digest fragment into pGEM3Zf(+) (Promega) in both orientations and maintained in *E. coli* strain JPA101. The single-stranded form of this clone was isolated and used in combination with synthetic deoxyoligonucleotides to introduce either three of four ribozyme catalytic units targeted against naturally occurring GUC and GUU sequences in the opposite sense CEV RNA strand. The method of introduction of the ribozyme sequences involved standards in vitro mutagenesis procedures. The target nucleotides are outlined in FIG. 1. The successful introduction of ribozyme sequences was analyzed by restriction endonuclease mapping and all constructs were assayed for catalytic activity by in vitro cleavage experiments. Cleavage experiments were completed by co-incubation of in vitro T7 RNA polymerase-generated RNA transcripts of the Ribozyme and appropriate CEV RNA target.

A 49 bp deletion (base 41–89) was introduced into all the constructs to satisfy GMAC requirements. The deletion was introduced by subcloning the remaining sequence as a blunt-ended BamH1-PstI restriction fragment into the SmaI site of pJ35SN. The orientation of the inserts relative to the 35S promoter was confirmed and then the promoter and construct was subcloned as a PstI fragment into the blunt-ended XhoI site of the broad host range plasmid pGA470. Triparental mating was employed to mobilize the constructs into *Agrobacterium tumefaciens.*

Figure 2:
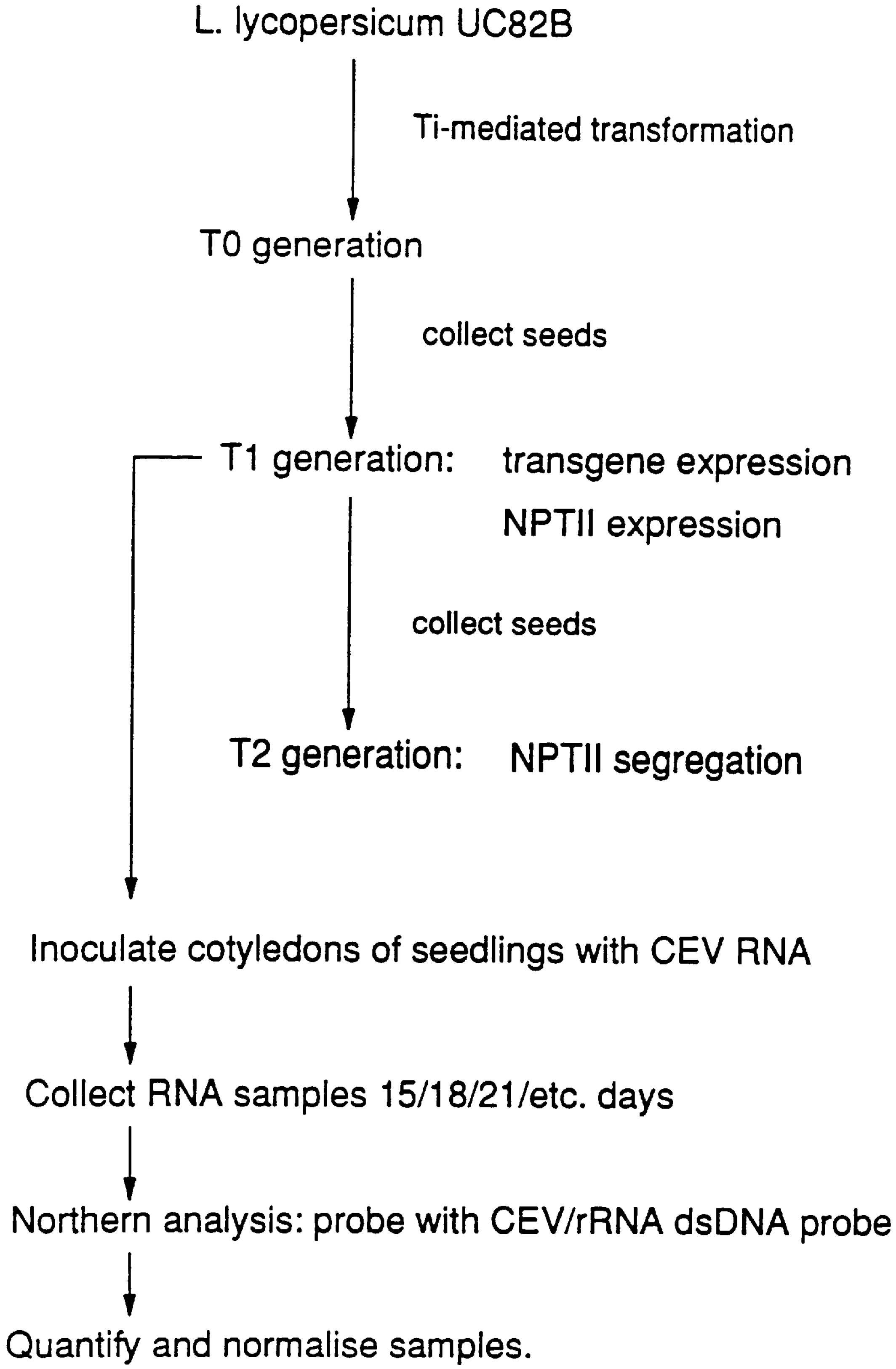
FIG. 2 is a schematic diagram showing the experimental outline of the project to determine the extent of viroid-resistance of transgenic tomato plants.

The *A. Tumefaciens* strain was used to inoculate leaf cuttings of *L. lycopersicum* UC82B. Individual genetically transformed plants were selected as kanamycin resistant regenerants ($T_0$ generation) and were transferred to a glass-house to allow fruiting and subsequent seed collection. The progeny of the T0 generation (T1 generation) were cultivated in glasshouses and analyzed for expression of the appropriate As or Ribozyme RNA and linkage with the expression of the kanamycin resistance gene (nptlI). Plants that were detected to be expressing the As or Ribozyme RNA by Northern hybridization and the nptlI gene by enzyme assay were allowed to fruit and seed collected. Plants from populations of the T2 generation of each of the As or Ribozyme-expressing/npt1I+T1 plants were screened for npt1I expression. Those T2 populations that were 100% npt1I + were assumed to be derived from parents that were homozygous for the transgenes and seeds were collected from those T1 plants. The susceptibility of As and Ribozyme-expressing plants to CEV infection was assayed as outlined in FIG. 2.

RESULTS

The initial experiment involved the challenge of 5 populations of transgenic plants consisting of four individual plants of one family from each of the constructs outlined in FIG. 1. Where several independent homozygotes were obtained for a construct the family expressing the highest level of transgene was selected for CEV challenging.

Figure 3A:
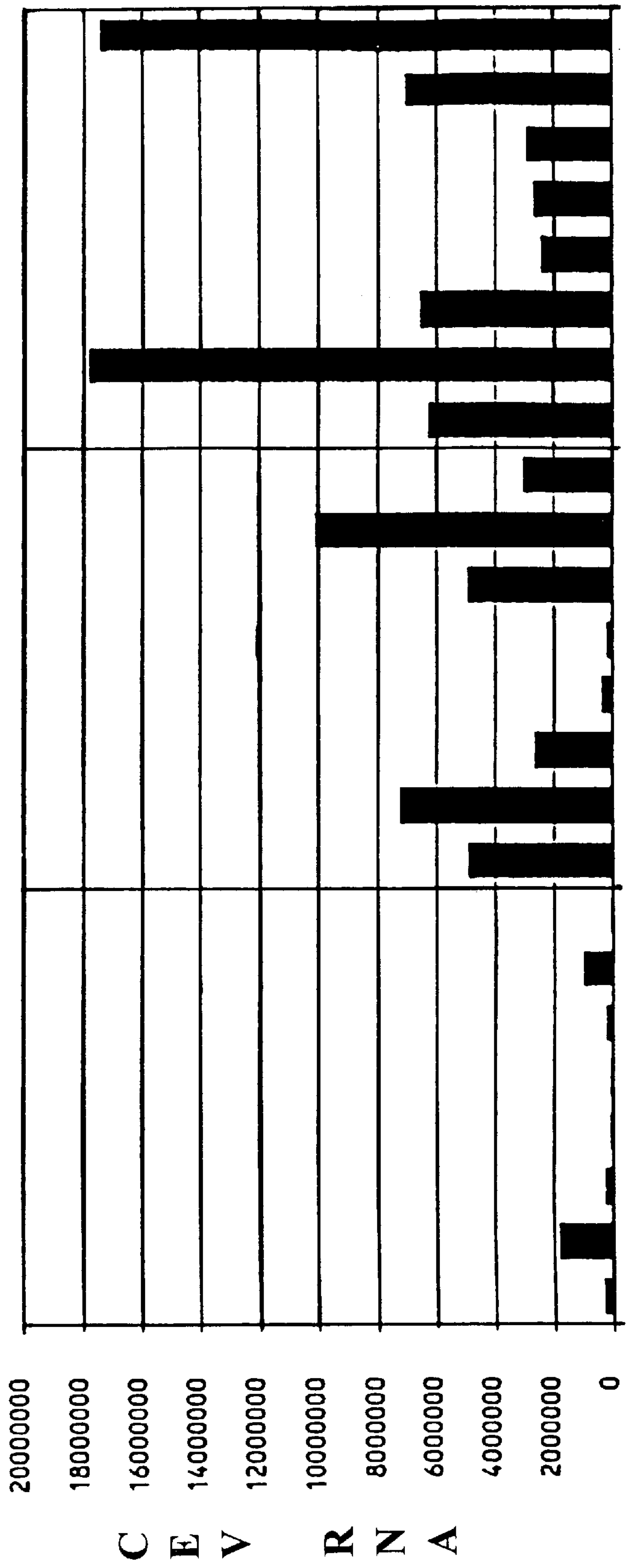
FIGS. 3A & B show the onset of viroid replication in transgenic plants as detected by northern blotting. The Y-axis shows arbitrary units indicating the intensity of the hybridization signal quantified using densitometric techniques. Each vertical bar represents a single plant at each time point.
Figure 3B:
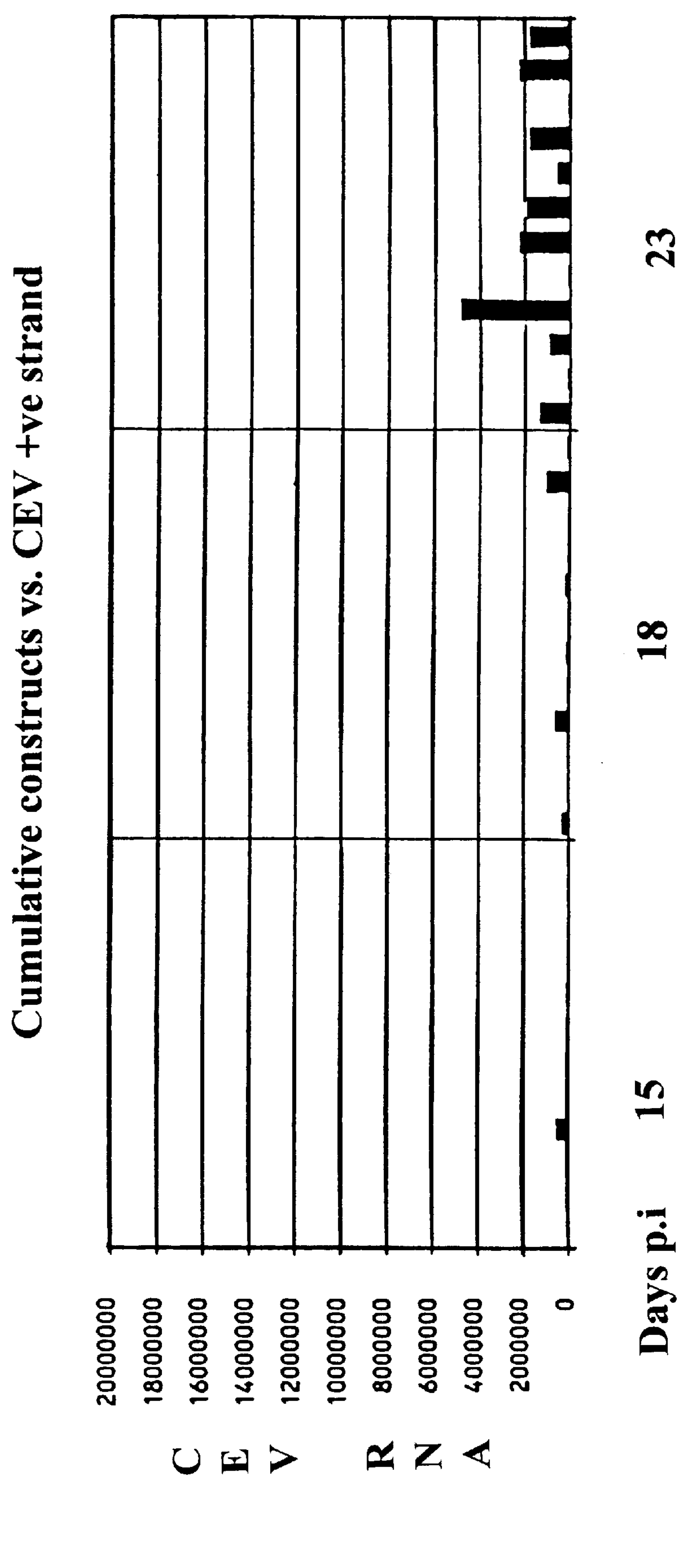

The quantitative analysis of the results is presented in FIG. 3 as the relative levels of CEV RNA detected by Northern hybridization. The Figure shows the results for all 4 plants of each family at 15, 18 and 23 days post inoculation (p.i.). The results are presented in groups of the targeted CEV RNA, i.e. those constructs targeting the positive strand and those constructs targeting the negative strand.

At the first time point CEV RNA is detectable in 5/8 of the plants containing transgenes targeting the positive strand where only 1/12 plants of the population containing transgenes targeting the negative strand had detectable CEV RNA. At 18 days p.i. all the plants of the former population had detectable CEV RNA, the highest levels were in the order of a ten fold increase on the levels detected in the plants expressing transgenes targeting the negative RNA strand. Inspection of the results of RNA levels detected at 23 days p.i. clearly shows that all the positive RNA strand-targeting plants contain relatively high levels of CEV RNA and the mean value is significantly greater than the level reached in any of the negative RNA strand-targeting plants. At 23 days p.i., 3/12 of the plants of this latter population still have no detectable CEV RNA.

Construction of antisense and ribozyme genes.

All routine DNA manipulations were as described in Sambrook et al. (1989). The CEV Australian isolate (CEV A) cDNA clone was obtained from Dr. P. Keese, CSIRO Division of Plant Industry, Canberra, Australia. The 371 bp CEV cDNA was subcloned as a BamHI fragement into BamHI-digested pGEM3Zf (+) DNA (Promega) and recombinant plasmids isolated and designated pCEV10 or pCEV11 depending if the insert was in the sense or antisense orientation to the T7 RNA polymerase promoter respectively. Either three or four ribozyme catalytic domains (Haseloff and Gerlach, 1988) were introduced sequentially by oligonucleotide site directed mutagenesis (Kunkel et al. 1987) of the appropriate pCEV plasmid. Four ribozymes were introduced into pCEV11 (FIG. 1) targeting naturally occurring GUC sequences within the CEV positive RNA strand at genomic co-ordinates 116, 144, 185 and 368 (Visvader et al., 1982). pCEV10 was mutagenised to include ribozymes targeting triplets in the CEV negative strand at position 198 (GUU), 243 (GUC) and 270 (GUU). A) second pCEV10-derived ribozyme was prepared by the introduction of a further catalytic sequence to the above ribozyme targeting the GUU triplet at position 90. The integrity of all ribozyme constructs was confirmed by DNA sequence analysis.

A long ribozyme targeting the TMV RNA polymerase gene was used for the completion of in vitro cleavage of TMV RNA to serve as a comparison for the analysis of the kinetics of the CEV ribozymes. The TMV long ribozyme was prepared by the introduction of three hammerhead catalytic domains into the TMV cDNA clone of the genomic 5' sequence, pTMV. pTMV was derived by subcloning a 999 bp SacI-XbaI fragment from a TMV U1 isolate cDNA clone encompassing the 5' 1004 nucleotides, pTMV (gift from W. O. Dawson, University of California, Riverside, USA), into pGEM3Zf(+). Transcription of the resultant TMV ribozyme gene, termed pTMV3Rz produced a ribozyme that targeted the TMV genomic-sense RNA molecule at GUC sequences at TMV co-ordinates 119, 137 and 159.

In vitro ribozyme cleavage reactions.

$^{32}$P-labelled target RNA was prepared by in vitro run-off transcription reactions (Melton et al., 1984) using T7 RNA polymerase and XbaI-linearized pCEV10 and pCEV11 DNA to produce positive and negative strand CEV RNA respectively. Similarly, ribozyme genes were linearized by XbaI digestion and unlabelled transcripts prepared as above. The TMV ribozyme and target RNA were prepared by transcription of PvuII or XbaI-linearized pTMV3Rz or pTMV respectively. In vitro ribozyme cleavage reactions were carried out and analyzed by electrophoresis in 7% polyacrylamide, 7 M urea gels and autoradiography as described in Perriman et al. (1992). Radiolabelled RNA bands were located by autoradiography and quantified by liquid scintillation counting.

Tomato transformation.

The five antisense and long ribozyme constructs were subclones as SmaI-blunt ended-PstI and blunt ended PstI fragments from pGEM3Zf(+) into the SmaI site of pJ35SN. This cloning method resulted in a 49 bp deletion of the CEV cDNA from genomic position 41–89 in order to reduce the viroid cDNA to less than full-genomic length. This was to avoid construction of transgenic plants that potentially could produce infectious viroid from an integrated gene, particularly in the case of the antisense genes. All constructs were then subcloned as blunt-ended PstI fragments into the blunt-ended XhoI site of the plant transformation vector pGA470, the antisense and long ribozyme genes then contained the CaMV 35S promoter sequence from pJ35SN at the 5' end and the nos gene polyadenylation sequence at the 3' end. The recombinant constructs were used to transform Agrobacterium tumefacians and transformants containing the correct recombinant plasmids identified by Southern blotting. L. lycopersicon cv. UC82B was transformed with the five constructs by the procedure described by Fillatti et al. (1987).

Transformed plant tissue was selected on the basis of the kanamycin-resistance phenotype conferred by the nptII gene of pGA470. Once regenerated, seedlings from independent transformants were transferred to glasshouses to set seed. All regenerants to this $T_0$ generation were screened for expression of the transgene by northern blotting and for nptII gene expression by a phosphotransferase dot blot assay method (McDonnell et al., 1987). Fruit from plants in which expression of both genes was detected was collected and seeds isolated by mild treatment of the fruit with dilute HCl (1/20 dilution of concentrated HCl in deionized water). $T_1$ seedlings were generated from the harvested seeds and were in turn screened for transgene and nptII gene expression as above. Sufficient seedlings were screened in order to determine if an approximate 3:1 transgene segregation ratio was occurring. Seeds were collected from those $T_1$ plants that were expressing the transgene and were members of a population where the transgene segregated at approximately 3:1. From these plants $T_2$ seedlings were generated and screened for nptII expression to determine if they were derived from a homozygote or hemizygous $T_1$ parent. At least 10 seedlings were screened and shown to be positive for the marker gene before a population was deemed likely to have been derived from a homozygous $T_1$ parent. Once identified, $T_1$ homozygotes were propagated and seed banks prepared for viroid inoculation experiments.

Nucleic acid extraction.

Total nucleic acid was prepared from tomato leaves by grinding 100 mg of tissue in a 1.5 mL microcentrifuge tube containing 200 $\mu$l of extraction buffer [2.5:1.25:0.025 TE3D{10% w/v) Nonadet P-40, 15% lithium dodecyl sulphate, 10% sodium deoxycholate, 2 mM EDTA, 20 mM Tris-HCl pH8.0}: Phenol solution: β-mercaptoethanol] with a glass rod. When the material was ground to a paste, 200 $\mu$l of 3 M ammonium acetate and 150 $\mu$l of chloroform:isoamyl alcohol (24:1) was added, the tub capped and vortexed for 1 minute. The aqueous phase was recovered and placed in a fresh tube following centrifugation of the leaf extract at 12000 g for 10 minutes at 4° C. The required nucleic acid fraction was prepared from this extract by differential precipitation. For the recovery of total RNA for detection of transgene transcripts the recovered solution was adjusted for 2 M lithium chloride and incubated at −20° C. for 2 hours. The insoluble RNA was recovered by centrifugation for 12000 g for 10 minutes at 4° C. The pellet was washed in 70% ethanol, dried in vacuo and resuspended in 10 $\mu$l of DEPC-treated sterile double-distilled water. For the purposes of detecting viroid and mRNA total nucleic acid samples were required as the rod-like nature of the viroid RNA ensures it remain soluble in 2 M lithium chloride. Total nucleic acid was prepared by the addition of 0.1 vol. 3 M sodium acetate (pH5.2) and 2 volumes 100% ethanol followed by incubation and centrifugation as for the total RNA preparation procedure.

Northern Blotting.

1/10 of the RNA and total nucleic acid samples extracted from 100 mg of leaf tissue were analyzed by electrophoresis through 1.2% agarose gels containing formaldehyde as described by Sambrook et al. (1989). Samples were denatured in formamide buffer containing 1 $\mu$g/mL ethidium bromide to allow visualization of the nucleic acid immediately after electrophoresis. Gels were washed in deionized water for 1 hour followed by further soaking in 2X SSC for 30 minutes. The nucleic acid was transferred to Hybond-N[30] membranes (Amerhsam, UK) by capillary blotting in 20X SSC for at least 8 hours. The nucleic acid was cross-linked to the membrane by UV treatment with a Stratalinker (Stratagene) according to the manufacturers instructions. Following cross-linking, the membrane was rubbed vigorously with a gloved finger for several minutes to remove residual agarose.

All filters were prehybridized in 20 mLs of hybridization solution [3X SSC, 0.5% (w/v) SDS, 5X Denhardt's reagent, 50% (v/v) de-ionized formamide, 100 $\mu$g/mL sheared, denatured herring sperm DNA ] in a large Hybaid hybridization tube at 45° C. for 3 hours. All radiolabelled DNA hybridization probes were prepared by oligonucleotide priming of a gel-purified DNA restriction fragment using an Amerhsam Multi-prime kit according to the manufacturers instructions. The radiolabelled DNA was precipitated from the labelling reaction, resuspended in TE buffer, boiled for 4 minutes and added to the prehybridized filter in 10 mLs for hybridization solution. Hybridization was allowed to proceed at 42° C. for 18 hours. The filters were washed at 60° C. in a succession of 2X SSC, 0.1% (w/v) SDS for 15 minutes and twice in 0.2X SSC, 0.1% (w/v) SDS for 30 minutes each. For the detection of the expression of transgenes encoding by CEV antisense or long ribozyme or viroid RNA at 371 bp gel-purified BamHI fragment of the CEV cDNA was used as a probe template. For secondary probing of blots for loading correction a 9 kb EcoRI-fragment representing a portion of the rDNA operon of Triticum aestivum, prepared from the clone pTA71 (Gerlach & Bedbrook, 1979), was used for probe preparation. This latter probe hybridized strongly with the tomato 18 s and 26 s rRNA. Counter probing was completed by keeping the initially probed blot damp during exposure in the phosphor cassettes and then repeating the prehybridizing and hybridizing with the second probe as above. The probe DNA bounded to the membranes was visualized by exposure of the membranes to a phosphor storage screen followed by processing of the screen in a Phosphorimager (Molecular Dynamics) according to the manufacturers instructions.

Preparation of infectious CEV RNA and plant inoculations.

All plants for inoculations were maintained at 30° C. with a 16 hr day and 8 hour night photoperiod. All inoculations were completed by dusting the fully-expanded cotyledons with carborundum followed by the application of 0.5 $\mu$l of the appropriate RNA solution and gently rubbing with a gloved finger. Infectious CEV RNA was isolated from CEV-inoculated Lycopersicon esculentum Mill cv. Rutgers as described by Rigden and Rezaian (1982). The purified CEV RNA was analyzed and titrated for infectivity by infection of four independent populations of four L. lycopersicon cv. UC82B plants with dilutions of the viroid RNA. In parallel, a population of L. esculentum Mill cv. Rutgers plants was infected to monitor symptom development.

Analysis of viroid RNA replication in CEV-infected transgenic tomatoes.

Populations of wild type and the various transgenic plans were maintained and inoculated as described above. At specific intervals after inoculation approximately 100 mg leaf samples were taken from the oldest leaf on each plant using a scalpel blade that had previously been soaked in 1 M sodium hydroxide and rinsed in sterile double-distilled water. Total nucleic acid was isolated from the leaf tissue as soon as possible after sample harvesting. The total nucleic acid samples and a standard sample of CEV-infected plant total nucleic acid were analyzed by northern blotting with CEV cDNA probe. Quantitative values were obtained for all CEV signal present using the software supplied with the Molecular Dynamics Phosphorimager. The filters were subsequently probed with the rDNA probe and the level of 26 s rRNA in each sample was quantitated. The values were adjusted for hybridization variation between filters by normalization of the value of the CEV and 26 s rRNA signal in the standard sample on each filter with the mean level of either all the standard CEV signal or the standard 26 s rRNA signal values as appropriate. These correction factors were applied to each sample value within each filter to standardize the hybridization signal throughout the experiment. The sample loading was equalized by determining the correction factor for each 26 s rRNA value from the mean value of all the 26 s rRNA values. This was then used to adjust the CEV values within each sample. The final result for each time point post inoculation was calculated as an average for the population and presented as a histogram. All data storage and manipulations were completed using the Excel spreadsheet software (Microsoft).

In Vitro Cleavage activity of CEV ribozymes.

Figure 4:
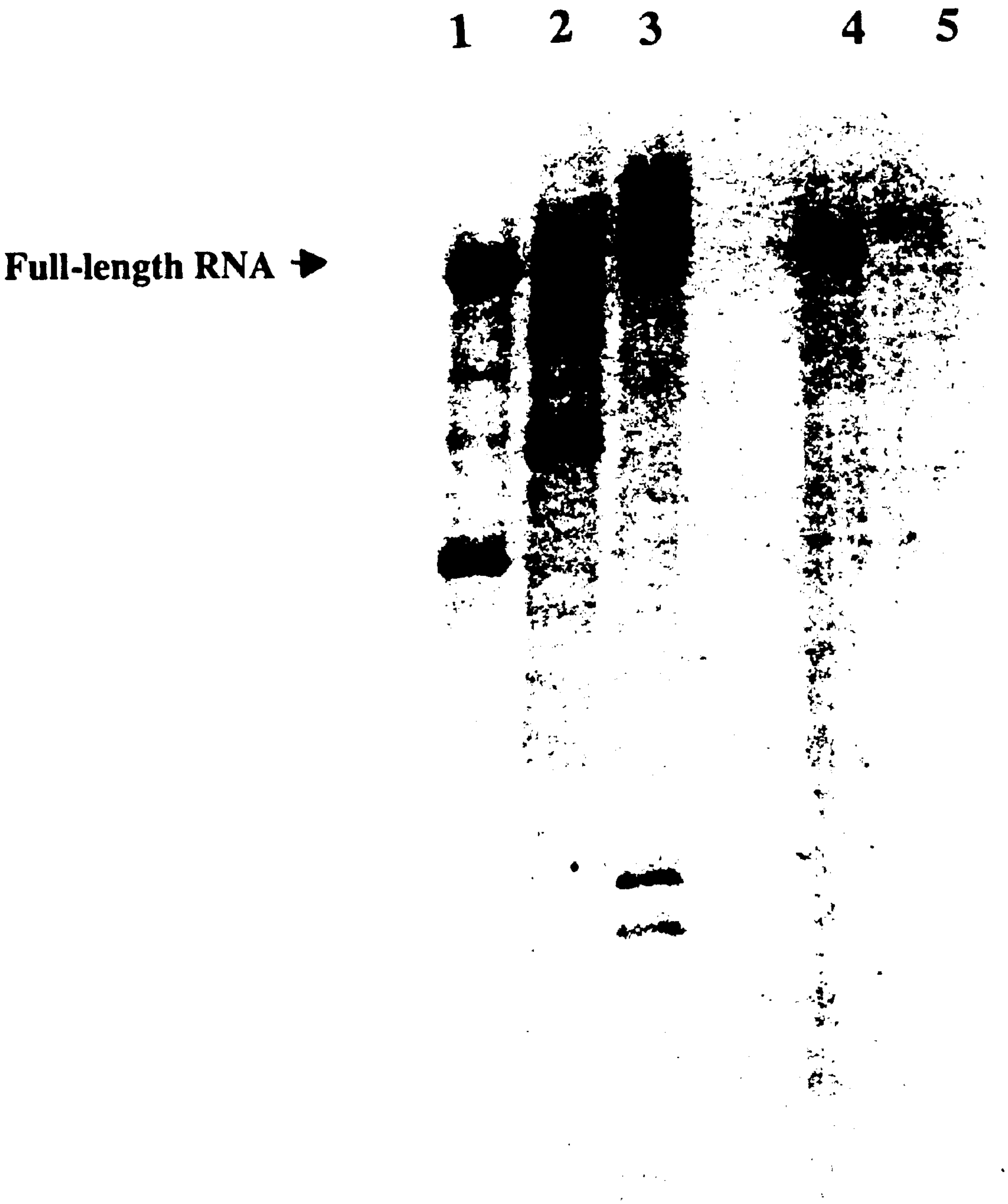
FIG. 4 is an autoradiograph of PAGE analysis of in vitro cleavage of synthetic CEV RNA by CEV ribozymes. Lanes 1 and 2 shows the cleavage products of negative strand RNA incubated with a 3 and 4 hammerhead ribozyme-containing RNA respectively [3Rz(−) and 4RZ(−)]. Lane 3 shows cleavage products of CEV positive strand RNA incubated with a 3 hammerhead ribozyme-containing RNA [3RZ(+)]. Lanes 4 and 5 show full-length CEV negative and positive RNA incubated in the absence of ribozyme RNA.
Figure 5:
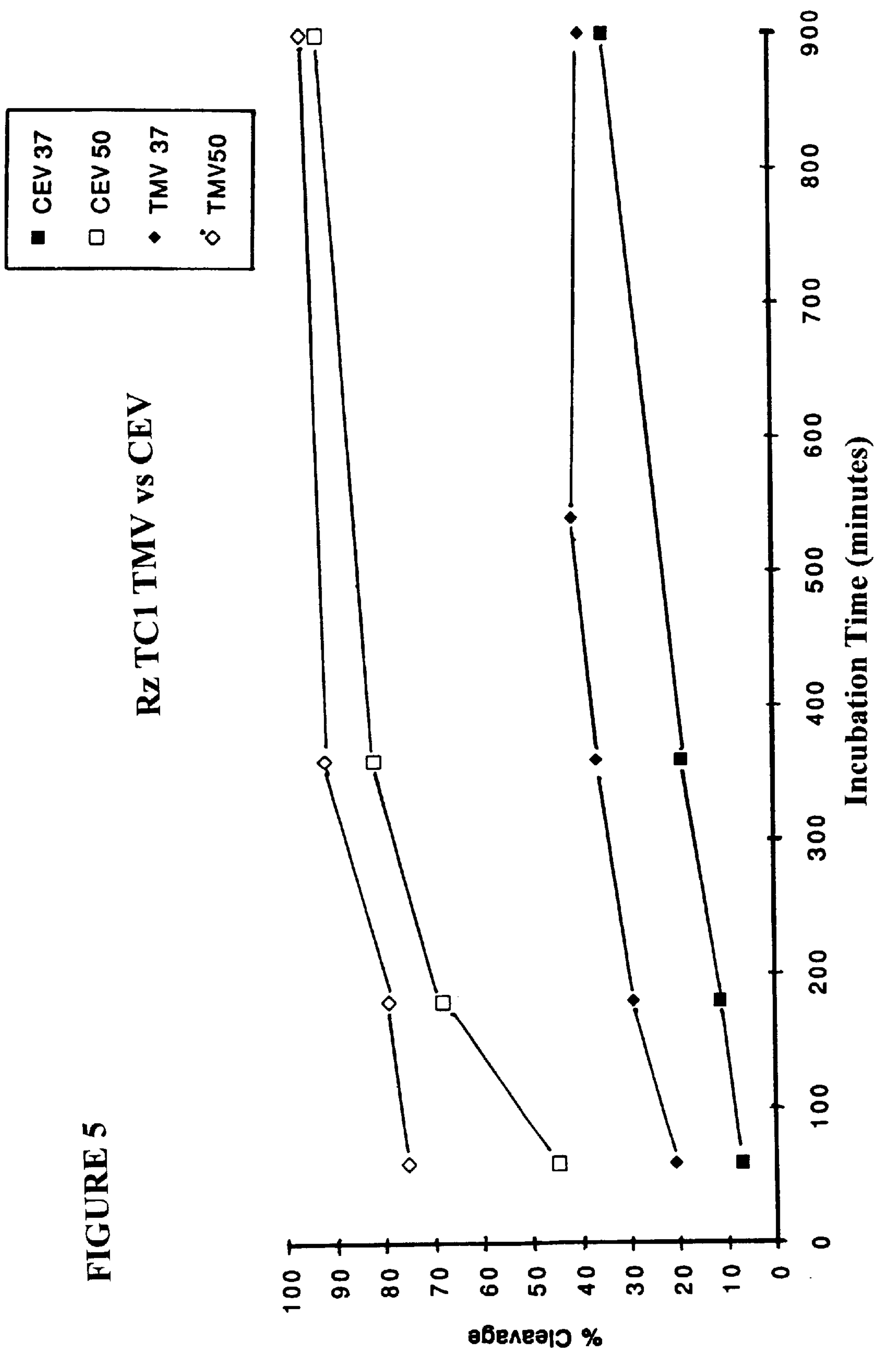
FIG. 5 is a graphical representation showing the onset of viroid replication in transgenic plants as detected by Northern blotting. In vitro cleavage efficiencies of the CEV 3Rz(+) and TMV3Rz and the appropriate RNA substrate are shown. The data shows time courses of cleavage for the two ribozymes over a 900 minute period at 37° C. and 50° C. Each time point is the average of four independent experiments.

The ribozymes designed to hydrolyse sequences within either the CEV positive or negative RNA strand (FIG. 1) were constructed and the DNA sequence analyzed to confirm that the catalytic domains had been introduced correctly. In vitro generated RNA transcripts of the ribozyme genes were then tested for catalytic activity by the completion of in vitro cleavage of CEV in vitro RNA transcripts. FIG. 4 shows that incubation of all the CEV ribozyme RNAs with the appropriate CEV RNA target results in at least partial cleavage of that target RNA into the expected RNA products. In order to determine if the CEV targets were particularly recalcitrant to formation of an RNA duplex and consequent hydrolysis due to their extensive intramolecular base pairing, comparisons of the kinetics of cleavage were made with another long ribozyme/target RNA combination, TMV and TMV3Rz. A time course of cleavage was completed four times for each target at 37° C. and 502 C. (FIG. 5). The results are presented as the proportion of the total substrate RNA that has been cleaved. At 37° C. the CEV substrate RNA cleavage remains at approximately 50% of that of the cleavage of the TMV substrate RNA until the final time point at which the proportion of RNA cleaved are similar at 35% and 39% for the CEV and TMV target respectively. To determine if the rates of cleavage of the two substrate could be enhanced by reducing the RNA secondary structure, cleavage reactions were also carried out at 50° C. The extent of cleavage after 60 minutes of incubation of both targets increased to four times the rates at 37° C. and CEV cleavage remained, as observed at 37° C., at approximately 50% of that of the TMV.

Analysis of Transgenic Plants.

Figure 6:
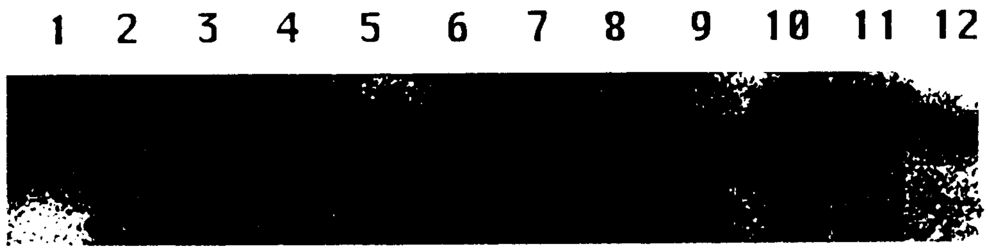
FIG. 6 is an autoradiograph of northern blot analysis of total RNA extracted from transgenic tomatoes transformed with the chimeric genes described in FIG. 1. An equally loaded agarose gel was transferred to an nylon filter and hybridized with CEV cDNA. Samples were prepared from 1–12) untransformed plants, transgenic plants expressing 3RZ(+)#1, 3Rz(+)#2, 3Rz(+)#3, 4Rz(−), As(+)#1, AS(+)#2, As(−)#1, As(−)#2, As(−)#3, 3Rz(−)#1, 3Rz(−)#2.

Kanamycin-resistant tomato $T_0$ seedlings were selected from the initial tomato transformation experiments for each of the 5 CEV constructs. From those $T_0$ seedlings detected to be expressing CEV-derived transgenes by northern blotting, T1 seedlings were prepared and analyzed for coincidence of nptII and transgene expression. Those $T_1$ plants identified as having the desire genotype were further characterized to be either homozygous or hemizygous for the transgenes by analysis of the segregation of the nptII gene in the $T_2$ population. At least 2 homozygous plants originating from independent primary transformation events were identified for each CEV transgene except for the 4Rz(−) for which only a single homozygote was identified. FIG. 6 shows the relative levels of the expression of the transgenes, as detected by northern blotting of an equally-loaded agarose gel, in the 11 identified homozygote plants. The level of transgene expression varied with the highest level in AS(+) #2 (lane 7) at approximately ten times that of the lowest level expression in 3Rz(−)#2 (lane 12). This wide variation in expression levels of transgenes, even of the same sequence, is a commonly observed phenomenon and is suggested to be dependent on the site of integration of the transgene in the plant chromosome.

Preparation of titration of CEV infectious RNA and Inoculation of Transgenic plants.

Viroid RNA was purified from 40 g of CEV A-infected L. esculentum leaf tissue and resuspended in water at a final concentration of 3 μg/mL. The infectivity of the RNA was assayed by inoculation of four populations, each containing four L. lycopersicon seedlings, with either 3 ng, 0.3 ng, 0.03 ng or 0.003 ng of CEV RNA per seedling. In addition, a L. lycopersicon population was mock inoculated and a population of L. esculentum Mill cv. Rutgers was inoculated with 3 ng of RNA per seedling to identify typical CEV symptoms. The levels of CEV RNA were determined by northern blot analysis of total nucleic acid extracted from the oldest leaf of each plant at five days intervals from 12 to 37 days post inoculation. All inoculations with CEV RNA resulted in productive infection and CEV RNA replication and all RNA challenges gave 100% productive infection rates by the final time point. The challenge of 0.03 ng per cotyledon was the lowest level that gave a productive infection onset in all members of the population at the same time point. No CEV RNA was detected in the mock inoculated plants and severe symptoms typical of CEV infection epinasty and stunting, were detected in the L. esculentum Mill cv. Rutgers population at 14 days post inoculation. Very mild symptoms were detected about half of the highest titre-infected L. lycopersicon population.

Figure 7A:
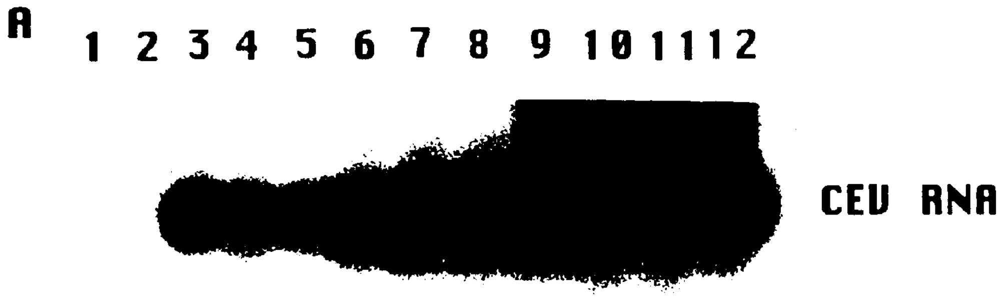
FIGS. 7A and 7B show examples of northern blot analysis of total nucleic acid extracts from transgenic tomato plants inoculated with CEV RNA.
Figure 7B:
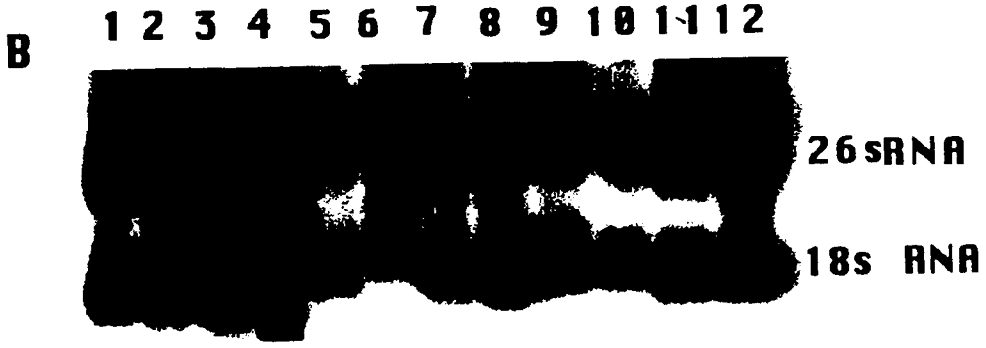

Populations of 8 plants for each of the 11 homozygous transgenic lines were challenged with 0.03 ng of CEV RNA; the lowest RNA inoculation previously determined to give reproducible viroid replication. The plants were sampled from the oldest leaf at 15, 19, 23, 28, 34 and 46 days post inoculation and RNA prepared and analyzed in batches immediately after tissue harvesting. FIG. 7 shows an examples of the northern blot results for 10 CEV-infected plant RNA samples and samples from 2 uninoculated plants that were obtained using the experimental procedure described. FIG. 7A shows the result of hybridization with the CEV probe and FIG. 7B shows duplicate samples hybridized with the rRNA DNA probe.

The process of RNA replication was analyzed in terms of two parameters, the onset of viroid replication and the levels of accumulation. The onset of replication is described as the proportion of plants in each population that shows viroid RNA levels greater or equal to levels detected in the similarly inoculated wild type population. The definition is designed to permit demonstration of variation from a fixed point in the rate of increase of the RNA replication in inoculated wild type plants to a detectable level. The determination of the levels of RNA accumulation was used to determine whether it was in any way reduced in comparison to the wild type plant levels.

The results of the analysis of the average levels of viroid RNA accumulation are shown in FIG. 8 in groups of glasses of constructs compared to the result obtained for the inoculated wild type population. The levels of CEV RNA were at the threshold of detection in only 2/8 of the wild type plants until 28 days post inoculation at which point the proportion of plants with detectable CEV RNA and the rate of accumulation increased in a linear manner over the remaining time points. Over the early time points there were inconsistencies in levels of CEV RNA in the same plant between time points. This was probably due to the fact that the levels of CEV RNA were close to the limit of detection and that, although exhaustive measures were taken to ensure consistency in sampling and hybridization analysis, there will be significant sampling errors when the signals are low. Analysis of the three independent transgenic families expressing antisense to the CEV negative RNA strand (FIG. 8A) all showed a lower proportion of infected plants and a significantly reduced level of CEV RNA levels over the first 23 days post inoculation. At 28 days post inoculation two of the three populations still had no detectable CEV RNA and the levels in these populations remained lower than the wild type levels throughout the remainder of the time course. The third population of plants expressing the antisense to the negative strand [As(−)190 3] showed CEV RNA levels and proportion of plants infected higher than the wild type at only one point. After that point the levels of both parameters for this third population are reduced in comparison to the wild type and reflect the reduced levels in the other two As(31) populations. The plants expressing the long ribozymes targeting the negative strand, 3Rz(−) #1 and #2 and 4Rz(−)π1 (FIG. 8B), all showed levels of CEV RNA below those detected in the wild type populations. The delay was maintained throughout the time course but was not as marked as that seen with the plants expressing the antisense gene targeting the negative CEV RNA strand. The only deviation from this pattern was the value for 3Rz(−)#2 at 23 days post inoculation at which point the viroid level was higher than the corresponding wild type levels and both the prior and later time point of the same population. Of the three populations expressing this class of constructs the transgene containing four catalytic sequences generally showed the greatest delay in onset of replication although the final level of accumulated RNA was intermediate between the two 3Rz(−) populations.

Figure 8A:
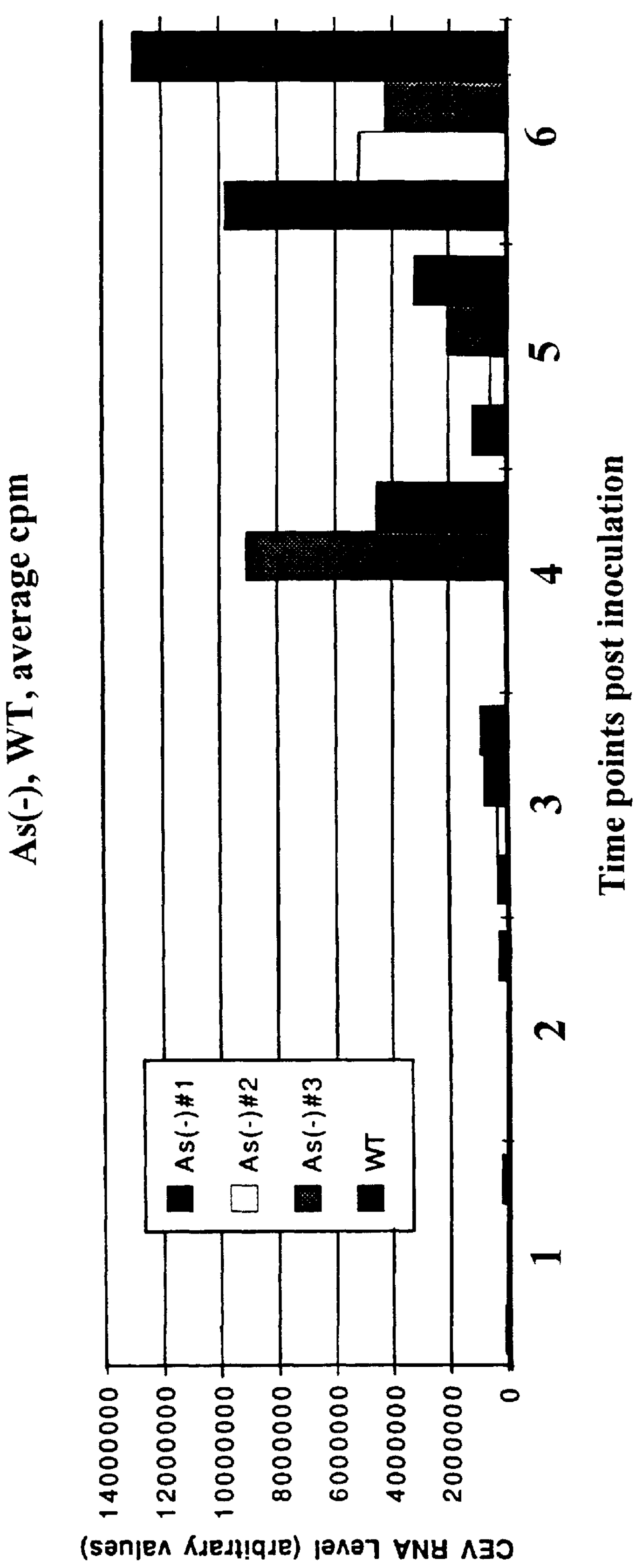
FIGS. 8A–8D show histograms representing the levels of CEV RNA, detected by northern blotting, in populations of low titre CEV-inoculated plants (0.03 ng CEV RNA/cotyledon) at time intervals over a course of infection. Each bar represents the average value for each time point for a given population following correction by hybridization and loading levels between sample batches. The Y axis is an arbitrary scale related to the detected intensity of hybridized radiolabelled probe. Each panel shows the time course for families derived from independent transformants for a class of constructs compared to the result from CEV inoculation of the wild type population.
Figure 8B:
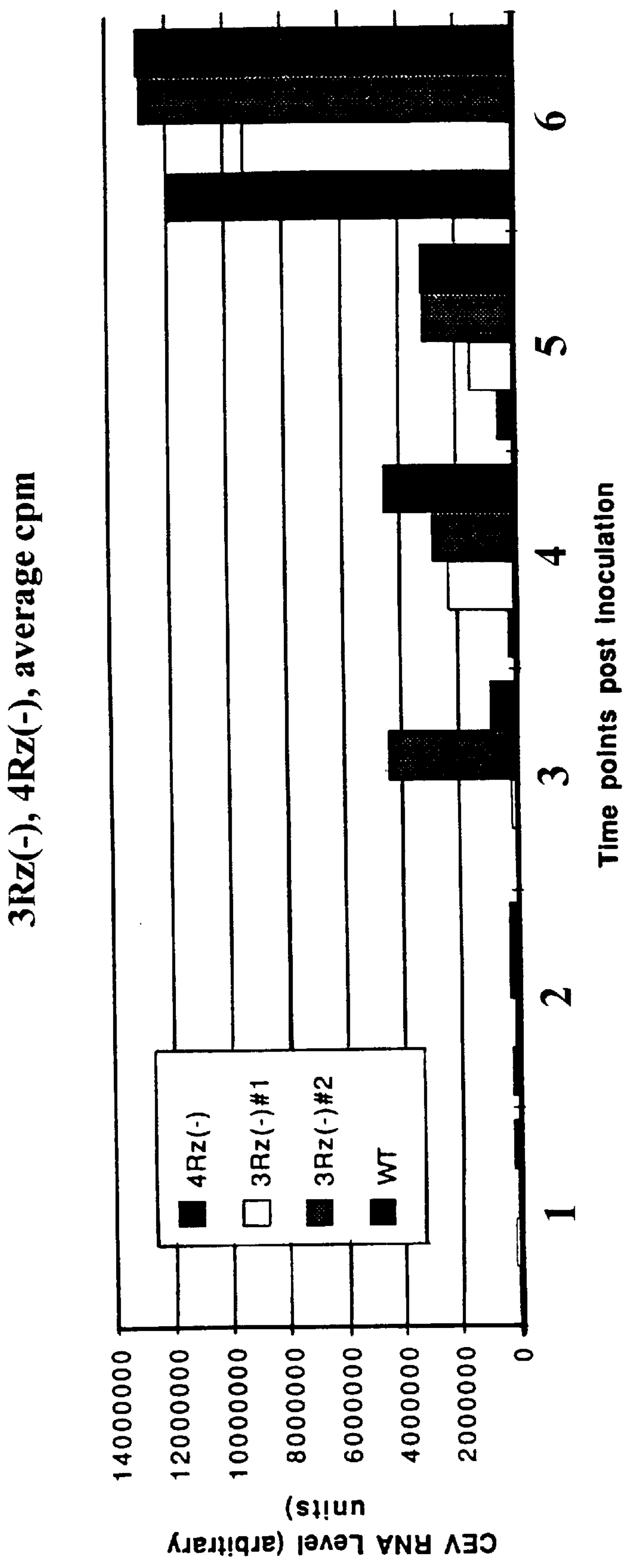
Figure 8C:
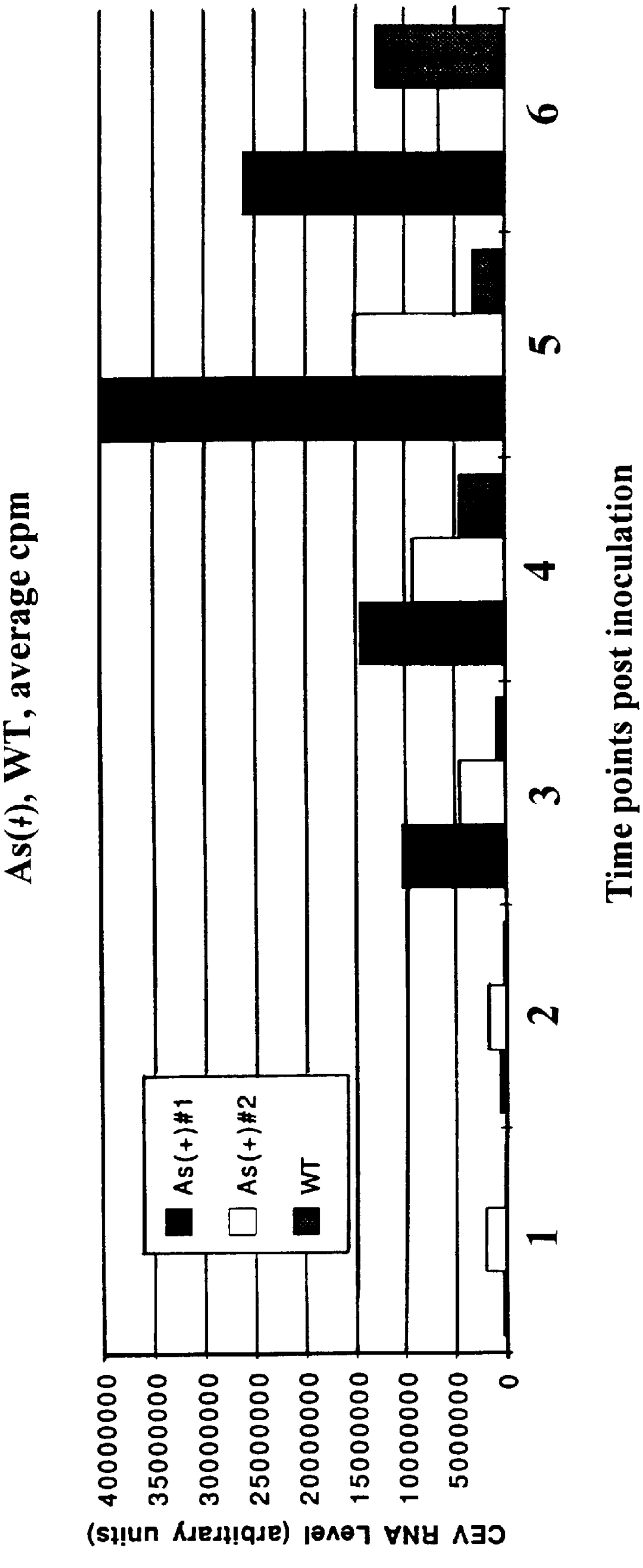
Figure 8D:
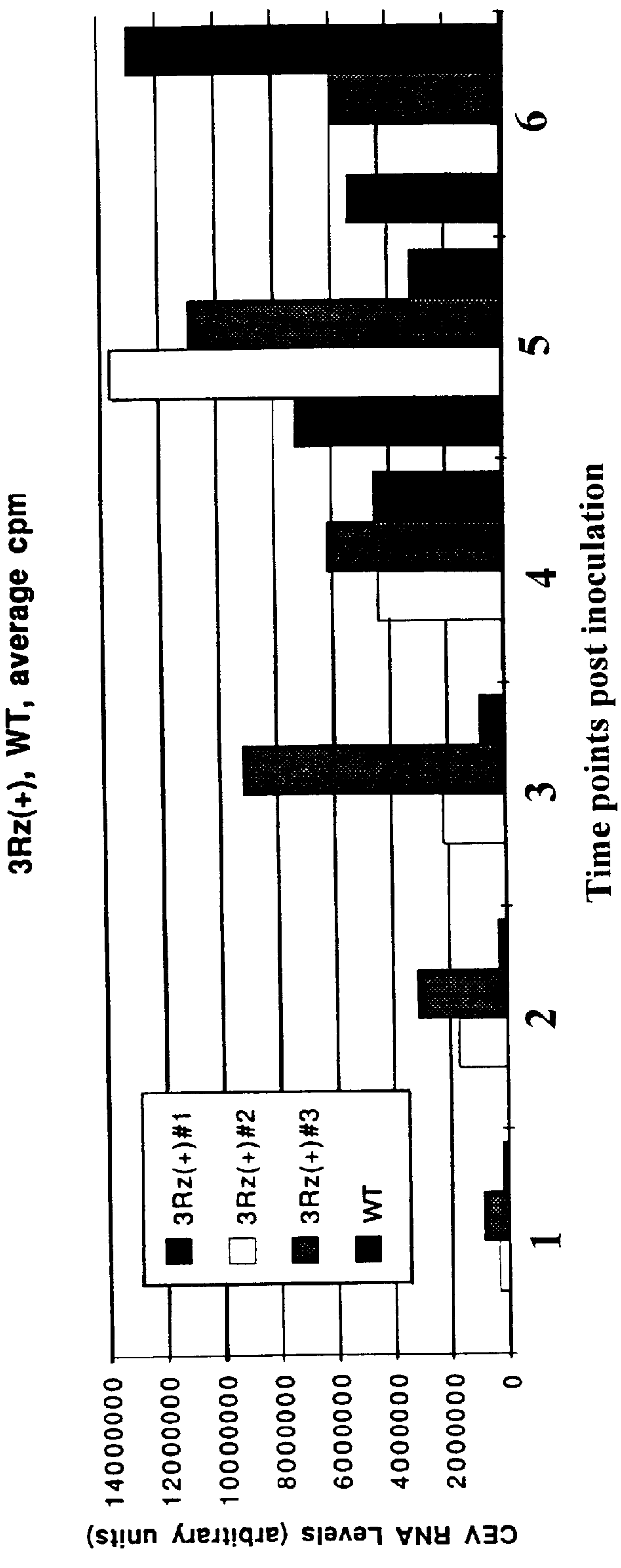

The CEV RNA replication and accumulation in plant populations expressing antisense to the CEV position strand (AS(+)#1 and AS(+)#2, [FIG. 8C] gave an unexpected result. The rate of onset of replication and levels accumulated were significantly greater than the wild type population with the maximum level between 3 and 8 times that of wild type reached at 34 days post inoculation rather than the end of the time course. The values for both As(30)#1 and #2 reduced between the last two time points with the CEV RNA values at 49 days post inoculation lower in the transgenic plants than in the wild type. Clearly, the latter time points cannot be compared in isolation as the CEV infection is more rapid in the AS(+) plants over the first five time points. Similarly, analysis of the result for the 3Rz(+) populations (FIG. 8D) shows higher levels of CEV RNA in the transgenic plants than in the wild type populations with a peak at 39 days pot inoculation followed by a reduction until the last time point. The CEV RNA levels that accumulated, although higher than those levels detected in the wild type population, were not as high as those levels observed in transgenic plants expressing antisense to the CEV positive strand.

Figure 9:
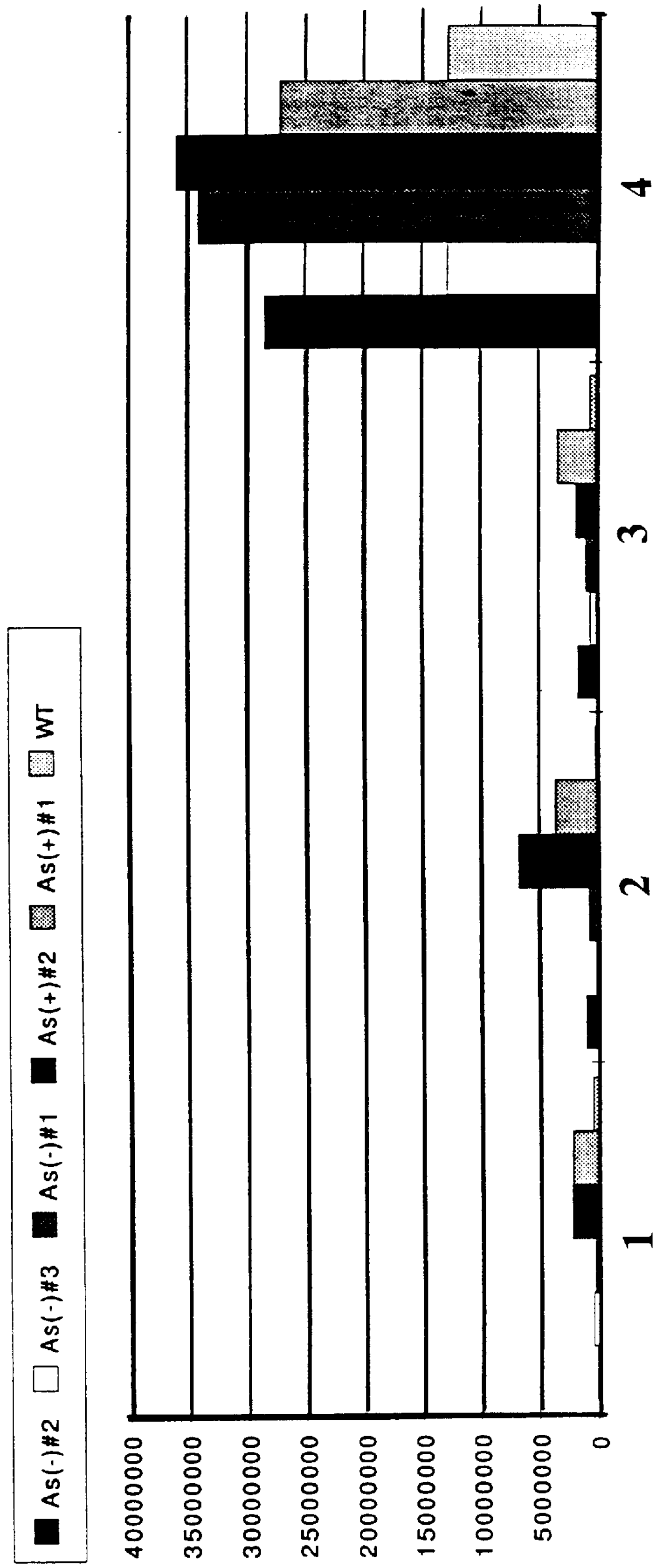
FIG. 9 shows average levels of CEV RNA detected in five populations of twelve plants expressing As(−)#1, As(−)#2, As(−)#3, As(+)#1 or As(+)#2 and untransformed *L. lycopersicon* cv UC82B that were inoculated with a high titre of CEV RNA (0.3 ng CEV RNA/cotyledon). Each bar represents the average value for each time point for a given population following correction for hybridization and loading levels between sample batches. The Y axis is an arbitrary scale related to the detected intensity of hybridized radiolabelled probe.

It was considered that the populations expressing the antisense genes were exhibiting the most marked effects of either apparent delay and reduction or enhancement of CEV replication and were subjected to a higher titre CEV RNA inoculation (0.3 ng CEV RNA per cotyledon) to further study the observations of the above experiment. FIG. 9 shows the levels of CEV RNA at 4 time points of the high titre inoculation of the transgenic populations expressing antisense genes or wild type. In contrast to the lower titre infection of kinetics of onset and levels of accumulation of CEV RNA do not differ significantly between any of the populations and the control plants. This result indicates that the delay seen in plants expressing either antisense or ribozymes targeting the viroid negative RNA strand is not obtained with a higher titre viroid inoculation.

DISCUSSION

A series of synthetic genes were constructed that when transcribed would produce either antisense or long ribozyme RNA sequences targeting either the CEV positive (genomic RNA strand) or the negative RNA strand synthesizes during replication. The range of constructs was prepared in order to evaluate the suitability of the various transgenes and the choice of target RNA in interfering with viroid replication. The experimental design was such that viroid replication could be analyzed directly with the use of an asymptomatic host rather than an observation of symptom development. This decision was made as the relationship between viroid RNA titre and symptom development is unknown and due to the desire to have an experimental readout that would detect quantitative effects on viroid replication. They would not be confused by secondary effects of symptom development.

The ribozyme constructs were prepared and demonstrated to be catalytically active in vitro. Further analysis of the long ribozyme targeting the positive CEV RNA strand was carried out by comparing the efficiency of cleavage with a TMV long ribozyme and target. The CEV ribozyme was less efficient than the TMV ribozyme with maximum cleavage rates approximately 50% of the TMV rate. The CEV ribozyme cleavage efficiency was enhanced several fold by incubation at a higher temperature suggesting the involvement of RNA secondary structure in the interference of cleavage at the lower temperature. This observation was not unexpected as the viroid RNA structure contains a high proportion of intramolecular base pairing conferring an almost double-stranded rod-like structure. It could be envisaged that it would be a thermodynamically unfavorable event for both the CEV target and long ribozyme target to form an RNA duplex with a complementary strand without some destabilization of the RNA structure. Although the in vitro cleavage rate of a pathogen at the early stage of an infection cycle may be effective at reducing propagation of the pathogen at later stages in the cycle.

Several independent transgenic homozygous plants were identified that expressed transgenes encoding the various antisense and long ribozyme sequences. The observation of the viroid replication and CEV RNA accumulation of the inoculated plants produced somewhat unexpected results. All homozygous populations expressing transgenes targeting the CEV negative RNA strand gave a degree of protection throughout the time course. In contrast to this observation, all plants expressing transgenes targeting the CEV positive strand appeared to support viroid replication at a significantly greater level than in the wild type or the transgenic plants expressing transgene targeting the negative CEV RNA. In both classes of constructs the addition of hammerhead ribozyme sequences to the antisense genes, although conferring catalytic activity in vitro, results in a decrease of the effects of the expression of the antisense genes. In all cases any difference in the effects on RNA replication or accumulation were lost following inoculation of the plants with a higher CEV RNA titre.

The protection conferred by transgenes expressing genes targeting the negative CEV RNA strand may reflect the lower intracellular concentration of that molecule, perhaps permitting the establishment of a more effective ratio of antisense/ribozyme:target. In addition, the detection of the viroid negative strand RNA in concatameric forms may indicate that the molecule adopts an alternative RNA secondary structure and is in a conformation more accessible to RNA intermolecular duplex formation. Alternatively, the vulnerability of the negative RNA strand may be due to its, at least transitory, location in a compartment of the cell such that it becomes accessible to the transgenic transcripts. The observation of the reduced effects by the long ribozyme targeting the same polarity CEV RNA strand may be the result of a destabilization of any potential duplex formation with the target RNA due to disruption of contiguous complementarity.

It is possible the apparent reduction in CEV RNA replication may not be the result of a primary interaction between transgenic RNA-CEV RNA but rather the result of an interaction between the transgenic transcript and the plant genome. The effect may be a form of the defective interfering (DI) particle phenomenon in that the transgenic RNA, less than genomic length, interacts with the plant component that normally is required for viroid replication. Effectively, the transgenic RNA sequesters and renders unavailable a component of the interaction normally required for CEV replication. The addition of the hammerhead sequences may reduce the interaction and thus permits a higher level of viroid replication.

The contrasting results observed in the plants expressing constructs targeting positive CEV RNA could also be the result of productive interactions between the transgenic RNA and the viroid RNA or plant host. The transgenic sequences may provide in trans stimulation of the viroid replication. At this stage it is difficult to envision what form of interaction could result in the upregulation of viroid replication given how little is known regarding the molecular details of viroid replication. Another possibility is that the transgenic RNA interacts with the host plant and prevents or moderates a host defense response. The reduction of the effect in the long ribozyme sequences could again be due to a perturbation of the RNA secondary structure by the hammerhead sequences, in turn altering resultant RNA duplex stability or binding associations.

These results show that expression of antisense or ribozyme genes, when targeted to the viroid negative strand, results in a delay in CEV RNA replication. This is the first description of any form of engineered viroid resistance and provides a good starting point from which to develop more efficient resistance genes. The observation of no apparent correlation in protection and transgene expression levels suggest that site of expression and transcript accumulation may be more important features. Second generation CEV transgenes might target RNA to the cell compartment in which viroids are though to accumulate and replicate, the nucleolus. Such transgenes may be introduced by targeting gene constructs under the control of RNA polymerase I promoters to the rRNA genes, a technique that has efficiently been completed in Saccharomyces cerevisiae. The observation of the apparent enhancement of viroid replication in plants expressing genes targeting the viroid positive RNA was unexpected and requires further investigation. This is in order to determine the nature of the effective trans complementation and its significance in viroid biology. In addition, this latter result is of particular importance with regard to careful design of transgenic experiments and thorough testing of plants in contained facilities.

These results are the first indication of the successful use of antisense genes and long ribozyme mediate resistance of a plant to a viroid pathogen. It provides a general approach to a range of viroid diseases and the mechanism can be exploited and extended to confer resistance to a number of economically important crops such as the protection of tomato, potato and avocado to CEV, PSTV and ASV, respectively amongst other plant infectious agents. Furthermore, the use resistance genes targeting the negative RNA strand or replicative form intermediate is unique and can be extended to target RNA virus pathogens of plants or animals, or other eukaryotes or prokaryotes.

Those skilled in the art will appreciate that the invention described herein is susceptible to variations and modification other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

Beachy, R. N., Loesch-Fries, S., and Tumer, N. E. (1990) Coat protein-mediated resistance against virus infection. Annu. Rev. Phytopathol. 28:451–474.

Bryant, J. (1992) Transgenic wheat plants: the end of the beginning. Tibtech 10:342–343.

Chrisley, L. A. (1991) Antisense Research and Development, 1:65–113.

Cuozzo, M., O'Connell, K. M., Kaniewski, W. Fang, R. -X., Chua, N. -H., and Tumer, N. E. (1988) Viral Protection in transgenic tobacco plants expressing the cucumber mosaic virus coat protein or its antisense RNA. Bio/Technology 6: 549–557.

Diener, T. O. 1987. "The Viruses. II. Series: The Viroids." (H. Fraenkel-Conrat and R. R. Wagner, Eds.). pp. 71–98. CRC Press, Boca Raton, Fla.

Edington, B. V. and Nelson R. S. (1992) Utilization of ribozymes in plants: Plant viral resistance. In "Gene Regulation: biology of antisense RNA and DNA" (R. P. Erickson and J. G. Izant, Eds.). pp. 209–222. Raven Press, New York.

Egholm, (1992) J. Am. Chem. Soc. 114:1895.

Fillatti. (1987) Biotechnology 5:726–730.

Gerlach, W. L., and Bedbrook, J. R. Cloning and characterization of ribosomal RNA genes from wheat and barley.

Golemboski, D. B., Lomonossoff, G. P., and Zaitlin, M. (1990) Plants transformed with a tobacco mosaic virus nonstructural gene sequence are resistant to the virus. Proc. Natl. Acad. Sci. USA 87:6311–6315.

Gordon et al. (1987) Bio/Technology 5:1183.

Hammer et al. 1985) Nature 315:680.

Hanvey et al., (1992) Science Vol. 258:1409–1548.

Haselhoff, J., and Gerlach, W. L. (1988) Simple RNA enzymes with new and highly specific endonuclease activities. Nature (London) 334:585–591.

Hemenway, C., Fang, R. -X., Kanieski, W. Chua, N. -H. and Turner, N. E. (1988) Analysis of the mechanism of protection in transgenic plants expressing the potato virus X coat protein or its antisense. EMBO J. 7:1273–1280.

Hutchins, C. J., Keese, P., Visvader, J. E., Rathjen, P. D., McInnes, J. L., and Symons, R. J. (1985) Comparison of multimeric plus and minus forms of viroids and virusoids. Plant Mol. Biol. 4:293–304.

Kunkel, T. A., Roberts, J. D., and Zakour, R. A. (1987) Rapid and efficient specific mutagenesis without phenotypic selection. Methods Enzymol. 154:257–382.

Kawchuk, L. M., Martin, R. R., McPherson, J. (1991) Sense and antisense RNA-mediated resistance to Potato Leafroll Virus in Russet Burbank potato plants. Mol. Plant-Microbe Interact. 4:247–253.

Macfarlane, S. A., and Davies, J. W. (1992) Plants transformed with a region of the 201-kilodalton replicase gene from pea early browning virus RNA1 are resistant to virus infection. Proc. Natl. Acad. Sci. USA 89:5829–5933.

Maliga, P. (1983) Towards plastid transformation in flowering plants. Tibtech 11:101–106.

McCall, M. (1992) Minimal sequence requirements for ribozyme activity. Proc. Natl. Acad. Sci. USA 89:5710–5714.

McDonnell, R. E., Clark, R. D., Smith, W. A., and Hinchee, M. A. (1987) A simplified method for the detection of neomycin phosphotransferase II activity in transformed plant tissues. Plant Mol. Biol. Biol. Rep. 5:380–386.

Melton, D. A., Krieg, P. A., Rebagliati, M. R., Maniatis, T., Zinn, K., and Green, M. R. (1984) Efficient in vitro synthesis of biologically active RNA and RNA hybridization probes from plasmids containing a bacteriophage SP6 promoter. Nucleic Acids Res. 12:7035–7056.

Nielson, (1991) Science 254:1497.

Perriman R., Delves, and Gerlach, W. L. (1992) Extended target-site specificity for a hammerhead ribozyme. Gene 113:157–163.

Pittius et al. (1988) PNAS 85:5874.

Rigden, J. E., and Rezaian, M. A. (1992) In vitro synthesis of an infectious viroid: analysis of the infectivity of monomeric linear CEV. Virology 189:201–206.

Saenger, W. (1984) Principles of Nucleic Acid Structure (Springer, New York).

Sanger, H. L. (1987) Viroid Replication of the "The Viroids" (T. O. Diener ed.) (Plenum Press, New York), pp.117–166.

Sambrook, J., Fritsch, E. F., and Maniatis, T. (1989) "Molecular Cloning: A Laboratory Manual." Cold Spring Harbor Laboratory, Cold Spring Harbor, N.Y.

Sanford, J. C., and Johnston, S. A. (1985) The concept of pathogen derived resistance: Deriving resistance genes from the parasites own genome. J. Theor. Biol. 113:395–405.

Sanger, H. L., Klotz, G., Reisner, D., Gross, H. J., and Kleinschmidt, A. K. (1976) Viroids are single-stranded covalently closed circular RNA molecules existing as highly base-paired rod-like structures. Proc. Natl. Acad. Sci. USA 73:3852–3856.

Shimamoto, K., Terada, R., Izawa, T., and Fujimoto, H. (1989) Fertile transgenic rice plants regenerated from transformed protoplasts. Nature 338:274–276.

Simons et al. (1987) Nature 328:530.

Simons et al. (1988) Bio/Technology 6:179.

Steinecke, P., Herget, T., and Scheier, P. H. (1992) Expression of Chimeric Ribozyme Gene Results in Endolytic Cleavage of Target mRNA and Concomitant Reduction in Gene Expression in vivo EMBO J. 11:1525–1530.

Symons, R. H. (1990) The fascination of low molecular weight pathogenic RNAs. Semin. Virol. 1:75–81.

Uhlmann, E. and Peyman A., (1990) Antisense Oligonucleotides: A New Therapeutic Principle. Chemical Reviews 90:543–584.

Van Brunt, J. Molecular Farming: Transgenic Animals as Bioreactors. Bio/Technology 6:1149–1154.

Visvader, J. E., Gould, A. R., Breuning, G. E., and Symons, R. H. (1982) Citrus exocortis viroid: Nucleotide sequence and secondary structure of an Australian isolate. FEBS Lett. 137:288–292.

What is claimed is:

1. A non-naturally occurring nucleic acid molecule which hybridizes to a (–) strand replicative intermediate of a plant virus, virusoid, or a viroid, wherein the nucleic acid molecule comprises a ribozyme.

2. The nucleic acid molecule of claim 1, wherein the nucleic acid molecule comprises a plurality of ribozymes wherein each ribozyme may be the same or different.

3. The nucleic acid molecule of claim 1, wherein the ribozyme is a hairpin ribozyme, a hammerhead ribozyme, a minizyme, or an RNAase P ribozyme.

4. The nucleic acid molecule of claim 3, wherein the ribozyme is a hammerhead ribozyme.

5. The nucleic acid molecule of claim 1, wherein the virus is a tobamovirus, a tobravirus, a hordeivirus, a potexvirus, a carlavirus, a potyvirus, a closterovirus, a tymovirus, a tombusvirus, a sobemovirus, or a luteovirus.

6. The nucleic acid molecule of claim 1, wherein the virus is a potato yellow dwarf virus, a cucumber mosaic virus, a tomato spotted wilt virus, a tomato mosaic virus, a potato virus X, a potato virus Y (PVY), a carnation latent virus, a tomato rattle virus, a pea early browning virus, a barley stripe mosaic virus, a turnip yellow mosaic virus, a barley yellow dwarf virus, a beet yellows virus, a potato leaf roll virus, a tomato bushy stunt virus, a southern bean mosaic virus, a maize chlorotic virus, beet necrotic yellow vein virus, or a tobacco necrosis virus.

7. The nucleic acid molecule of claim 1, wherein the viroid is avocado sunblotch viroid (ASBV), burdock stunt viroid (BSV), chrysanthemum chlorotic mottle viroid (CCMV), chrysanthemum stunt viroid (CSV), citrus exocortis viroid (CEV), coconut cadang-cadang viroid (CCCV), cucumber pale fruit viroid (CPFV), hop stunt viroid (HSV), potato-spindle tuber viroid (PSTV), tomato bunchy top viroid (TBTV), or tomato "planta macho" viroid (TPMV).

8. The non-naturally occurring nucleic acid molecule of claim 1, which hybridizes to a (–) strand replicative intermediate of the citrus exocortis viroid (CEV).

9. A DNA molecule which codes for the nucleic acid molecule of claim 1.

10. A transfer vector comprised of RNA or DNA containing a nucleotide sequence which on transcription gives rise to the nucleic acid molecule of claim 1.

11. A process for rendering a plant resistant to viral infection which comprises introducing into the plant a gene which on transcription gives rise to the nucleic acid molecule of claim 1.

12. The process of claim 11, wherein the introduction of the gene is made by genetic transformation of a part of the plant by a DNA molecule having a sequence coding for the nucleic acid molecule, followed by the regeneration of a transgenic plant.

13. The process of claim 12, wherein the transformation is carried out by the intermediary of *Agrobacterium tumefaciens* or *Agrobacterium rhizogenes.*

14. A process for rendering plant cells resistant to viral infection which comprises treating the plant cells with the nucleic acid molecule of claim 1.

15. The process of claim 14, wherein the plant cells are of *Lycopersicon lycopersicum.*

16. A method of interfering with the replication of a plant virus having a (–) replicative strand, which comprises contacting a plant cell with the nucleic acid molecule of claim 1 or the DNA molecule of claim 9 so as to thereby inhibit the replication of the plant virus in that cell.

* * * * *